(12) United States Patent
Pötter et al.

(10) Patent No.: US 9,200,043 B2
(45) Date of Patent: Dec. 1, 2015

(54) BIOCATALYTIC OXIDATION PROCESS WITH ALKL GENE PRODUCT

(75) Inventors: Markus Pötter, Münster (DE); Andreas Schmid, Dortmund (DE); Bruno Bühler, Dortmund (DE); Hans-Georg Hennemann, Marl (DE); Mattijs Kamiel Julsing, Dortmund (DE); Steffen Schaffer, Herten (DE); Thomas Haas, Münster (DE); Manfred Schrewe, Dortmund (DE); Sjef Cornelissen, Kopenhagen (DK); Martin Roos, Haltern am See (DE); Harald Häger, Lüdinghausen (DE)

(73) Assignee: Evonik Degussa GmbH, Essen (DE)

( * ) Notice: Subject to any disclaimer, the term of this patent is extended or adjusted under 35 U.S.C. 154(b) by 242 days.

(21) Appl. No.: 13/642,412

(22) PCT Filed: Mar. 15, 2011

(86) PCT No.: PCT/EP2011/053834
§ 371 (c)(1),
(2), (4) Date: Jan. 2, 2013

(87) PCT Pub. No.: WO2011/131420
PCT Pub. Date: Oct. 27, 2011

(65) Prior Publication Data
US 2013/0052700 A1   Feb. 28, 2013

(30) Foreign Application Priority Data
Apr. 20, 2010 (DE) .................. 10 2010 015 807

(51) Int. Cl.
| | | |
|---|---|---|
| C12P 13/00 | (2006.01) |
| C07K 14/21 | (2006.01) |
| C12P 7/02 | (2006.01) |
| C12P 7/24 | (2006.01) |
| C12P 7/42 | (2006.01) |
| C12P 7/62 | (2006.01) |
| C12P 7/64 | (2006.01) |

(52) U.S. Cl.
CPC . *C07K 14/21* (2013.01); *C12P 7/02* (2013.01); *C12P 7/24* (2013.01); *C12P 7/42* (2013.01); *C12P 7/62* (2013.01); *C12P 7/6436* (2013.01); *C12Y 114/15003* (2013.01)

(58) Field of Classification Search
CPC ............. C07K 14/21; C12P 7/02; C12P 7/24
USPC .................................. 435/134–136
See application file for complete search history.

(56) References Cited

U.S. PATENT DOCUMENTS

| | | | |
|---|---|---|---|
| 6,620,970 B2 | 9/2003 | Schiffer et al. |
| 6,639,108 B2 | 10/2003 | Schiffer et al. |
| 6,861,540 B2 | 3/2005 | Herwig et al. |
| 6,878,836 B2 | 4/2005 | Haas et al. |
| 7,030,052 B2 | 4/2006 | Stochniol et al. |
| 7,049,450 B2 | 5/2006 | Hofen et al. |
| 7,091,384 B2 | 8/2006 | Jaeger et al. |
| 7,157,610 B2 | 1/2007 | Hofen et al. |
| 7,195,748 B2 | 3/2007 | Jaeger et al. |
| 7,507,862 B2 | 3/2009 | Stochniol et al. |
| 7,754,778 B2 | 7/2010 | Knott et al. |
| 7,879,938 B2 | 2/2011 | Häger et al. |
| 7,923,225 B2 | 4/2011 | Mueller et al. |
| 8,216,813 B2 | 7/2012 | Thum et al. |
| 8,349,596 B2 | 1/2013 | Mueller et al. |
| 8,349,907 B2 | 1/2013 | Henning et al. |
| 8,399,658 B2 | 3/2013 | Hengstermann et al. |
| 8,404,470 B2 | 3/2013 | Thum et al. |
| 8,445,720 B2 | 5/2013 | Hannen et al. |
| 8,486,677 B2 | 7/2013 | Thum et al. |
| 8,604,227 B2 | 12/2013 | Petrat et al. |
| 8,796,000 B2 | 8/2014 | Thum et al. |
| 9,000,223 B2 | 4/2015 | Micoine et al. |
| 2002/0087036 A1 | 7/2002 | Haas et al. |
| 2003/0212298 A1 | 11/2003 | Brasse et al. |
| 2010/0068773 A1 | 3/2010 | Marx et al. |
| 2010/0167360 A1 | 7/2010 | Thum et al. |
| 2010/0190219 A1 | 7/2010 | Schaffer et al. |
| 2010/0190224 A1 | 7/2010 | Poetter et al. |
| 2010/0248325 A1 | 9/2010 | Eckstein et al. |
| 2010/0261237 A1 | 10/2010 | Verseck et al. |
| 2010/0266518 A1 | 10/2010 | Springer et al. |
| 2010/0291644 A1 | 11/2010 | Marx et al. |
| 2010/0324257 A1 | 12/2010 | Karau et al. |
| 2011/0039313 A1 | 2/2011 | Verseck et al. |
| 2011/0118433 A1 | 5/2011 | Pötter et al. |

(Continued)

FOREIGN PATENT DOCUMENTS

| | | |
|---|---|---|
| EP | 0 277 674 A1 | 8/1988 |
| EP | 0 502 524 A1 | 9/1992 |

(Continued)

OTHER PUBLICATIONS

U.S. Appl. No. 14/110,450, filed Oct. 8, 2013, Klasovsky, et al.
U.S. Appl. No. 14/126,607, filed Dec. 16, 2013, Haas, et al.
U.S. Appl. No. 14/000,067, filed Aug. 16, 2013, Erhardt, et al.
U.S. Appl. No. 14/000,028, filed Aug. 16, 2013, Erhardt, et al.
U.S. Appl. No. 14/077,750, filed Nov. 12, 2013, Schaffer, et al.
U.S. Appl. No. 13/721,481, filed Dec. 20, 2012, Gielen, et al.
U.S. Appl. No. 14/363,178, filed Jun. 5, 2014, Haas, et al.

(Continued)

*Primary Examiner* — Tekchand Saidha
(74) *Attorney, Agent, or Firm* — Oblon, McClelland, Maier & Neustadt, L.L.P.

(57) ABSTRACT

The invention provides a biocatalytic process for oxidation of organic compounds with the aid of an alkL gene product, and microorganisms used in this process.

25 Claims, 1 Drawing Sheet

(56) References Cited

U.S. PATENT DOCUMENTS

| | | |
|---|---|---|
| 2011/0118504 A1 | 5/2011 | Haas et al. |
| 2011/0171702 A1 | 7/2011 | Reinecke et al. |
| 2011/0189742 A1 | 8/2011 | Haas et al. |
| 2011/0251399 A1 | 10/2011 | Dingerdissen et al. |
| 2011/0257429 A1 | 10/2011 | Schraven et al. |
| 2011/0269977 A1 | 11/2011 | Dingerdissen et al. |
| 2012/0034665 A1 | 2/2012 | Haas et al. |
| 2012/0041216 A1 | 2/2012 | Sieber et al. |
| 2012/0071577 A1 | 3/2012 | Pfeffer et al. |
| 2012/0077932 A1 | 3/2012 | Pfeffer et al. |
| 2012/0245375 A1 | 9/2012 | Hannen et al. |
| 2012/0264182 A1 | 10/2012 | Reinecke et al. |
| 2012/0315366 A1 | 12/2012 | Zehnacker et al. |
| 2013/0035403 A1 | 2/2013 | Schaffer et al. |
| 2013/0092233 A1 | 4/2013 | Pawlik et al. |
| 2013/0130319 A1 | 5/2013 | Schaffer et al. |
| 2013/0165672 A1 | 6/2013 | Klasovsky et al. |
| 2013/0165685 A1 | 6/2013 | Hannen et al. |
| 2013/0183725 A1 | 7/2013 | Poetter et al. |
| 2013/0245276 A1 | 9/2013 | Klasovsky et al. |
| 2013/0299750 A1 | 11/2013 | Hermasch et al. |
| 2013/0331580 A1 | 12/2013 | Klasovsky et al. |
| 2014/0199736 A1 | 7/2014 | Köhler et al. |

FOREIGN PATENT DOCUMENTS

| | | |
|---|---|---|
| WO | 02/22845 A1 | 3/2002 |
| WO | 2009/077461 A1 | 6/2009 |

OTHER PUBLICATIONS

U.S. Appl. No. 14/363,165, filed Jun. 5, 2014, Pfeffer, et al.
U.S. Appl. No. 14/367,610, filed Jun. 20, 2014, Haas, et al.
U.S. Appl. No. 14/373,089, filed Jul. 18, 2014, Engel, et al.
U.S. Appl. No. 14/380,483, filed Aug. 22, 2014, Schiemann, et al.
S.A. Rothen et al.—"Tiotransformation of Octane by *E. coli* HB101[pGEc47] on Defined Medium: Octanoate Production and Product Inhibition", Biotechnology and Bioengineering, vol. 58, No. 4, May 20, 1998, pp. 356-365.
Olivier Favre-Bulle et al.—"Bioconversion of N-Octane to Octanoic Acid by a Recombinant *Escherichia coli* Cultured in a Two-Liquid Phase Bioreactor", Bio/Technology vol. 9, Apr. 1991, pp. 367-371.
Silke Schneider et al.—"Biocatalyst Engineering by Assembly of Fatty Acid Transport and Oxidation Activities for In Vivo Application of Cytochrome P-450$_{BM-3}$ Monooxygenase", Applied and Environmental Microbiology, vol. 64, No. 10, Oct. 1998, pp. 3784-3790.
Qi Chen et al.—"Physiological Changes and alk Gene Instability in *Pseudomonas oleovorans* during Induction and Expression of alk Genes", Journal of Bacteriology, vol. 178, No. 18, Sep. 1996, pp. 5508-5512.
Tracy M. Neher et al.—"*Pseudomonas fluorescens* ompW: plasmid localization and requirement for naphthalene uptake", Can. J. Microbiol, vol. 55, 2009, pp. 553-563.
Jan B. van Beilen et al.—"DNA sequence determination and functional characterization of the OCT-plasmid-encoded alkJKL genes of *Pseudomonas oleovorans*", Molecular Microbiology, 1992, vol. 6, No. 21, pp. 3121-3136.
Jan B. van Beilen et al.—"Analysis of *Pseudomonas putida* alkane-degradation gene clusters and flanking insertion sequences: evolution and regulation of the alk genes", Microbiology, 2001, vol. 147, pp. 1621-1630.
Jan B. van Beilen et al.—"Genetics of alkane oxidation of *Pseudomonas oleovorans*", Biodegradation vol. 5, 1994, pp. 161-174.
U.S. Appl. No. 14/233,505, filed Jan. 17, 2014, Poetter, et al.
U.S. Appl. No. 14/237,121, filed Feb. 4, 2014, Haas, et al.
U.S. Appl. No. 14/238,576, filed Feb. 12, 2014, Schaffer, et al.
U.S. Appl. No. 14/238,591, filed Feb. 12, 2014, Schaffer, et al.
U.S. Appl. No. 14/132,473, filed Dec. 18, 2013, Schaffer, et al.
U.S. Appl. No. 14/384,301, filed Sep. 10, 2014, Schaffer, et al.
U.S. Appl. No. 14/390,133, filed Oct. 2, 2014, Hennemann, et al.
U.S. Appl. No. 14/395,666, filed Oct. 20, 2014, Haas, et al.
U.S. Appl. No. 14/405,050, filed Dec. 2, 2014, Haas, et al.
U.S. Appl. No. 14/400,379, filed Nov. 11, 2014, Haas, et al.
Bernard Witholt et al., "Bioconversions of Aliphatic Compounds by *Pseudomonas oleovorans* in Multiphase Bioreactors: Background and Economic Potential", Tibtech, vol. 8, Feb. 1990, pp. 46-52.
Jonathan D. Van Hamme et al., "Recent Advances in Petroleum Microbiology", Microbiology and molecular biology reviews, vol. 67, No. 4, Dec. 2003, pp. 503-549.
M. Nieboer, J. Kingma and B. Witholt, The alkane oxidation system of *Pseudomonas oleovorans*: Induction of the alk genes in *Escherichia coli* W3110(pGEc47) affects membrane biogenesis and results in overexpression of alkane hydroxylase in a distinct cytoplasmic membrane subtraction, Molecular Microbiology, 1993, pp. 1039-1051.
U.S. Appl. No. 14/435,339, filed Apr. 13, 2015, Engel, et al.
U.S. Appl. No. 14/419,580, filed Feb. 4, 2015, Erhardt, et al.
U.S. Appl. No. 14/425,180, filed Mar. 2, 2015, Ortelt, et al.

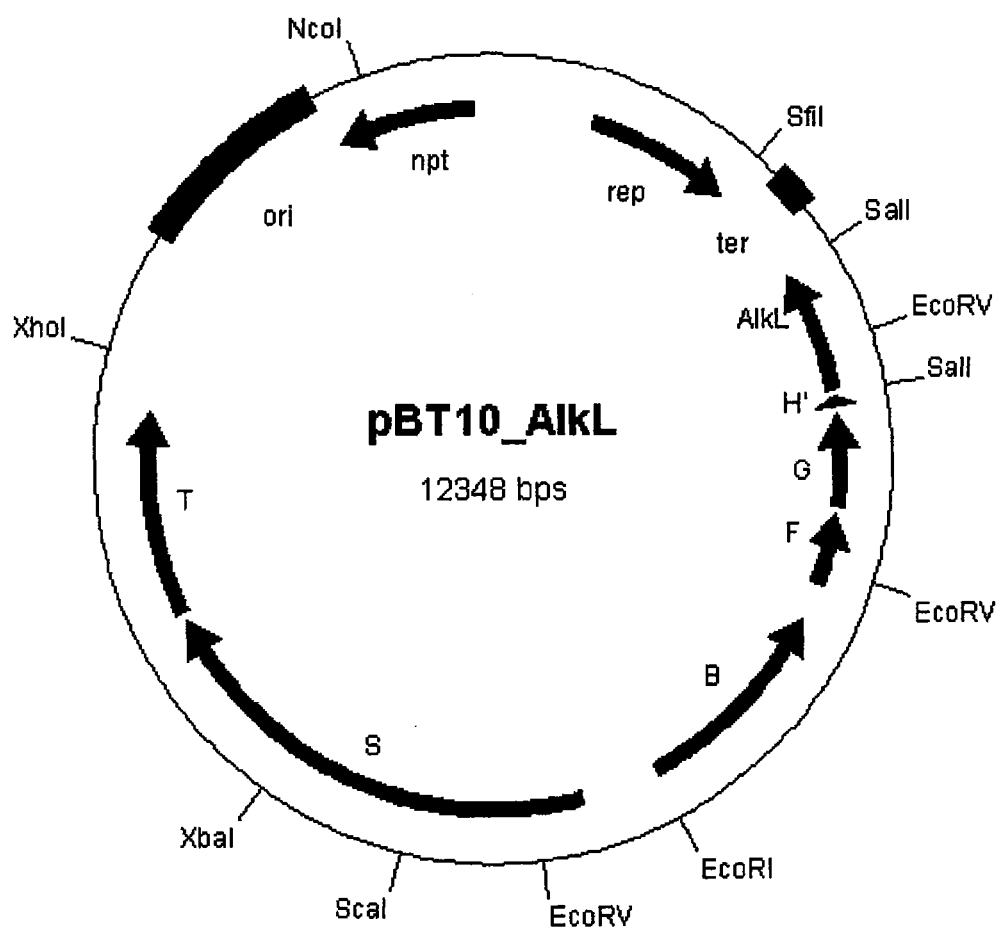

SEQUENCE LISTING

<160> NUMBER OF SEQ ID NOS: 8

<210> SEQ ID NO 1
<211> LENGTH: 693
<212> TYPE: DNA
<213> ORGANISM: Pseudomonas putida
<220> FEATURE:
<221> NAME/KEY: AlkL
<222> LOCATION: (1)..(693)
<220> FEATURE:
<221> NAME/KEY: CDS
<222> LOCATION: (1)..(693)

<400> SEQUENCE: 1

```
atg agt ttt tct aat tat aaa gta atc gcg atg ccg gtg ttg gtt gct      48
Met Ser Phe Ser Asn Tyr Lys Val Ile Ala Met Pro Val Leu Val Ala
1               5                  10                  15 aat ttt gtt ttg ggg gcg gcc act gca tgg gcg aat gaa aat tat ccg      96
Asn Phe Val Leu Gly Ala Ala Thr Ala Trp Ala Asn Glu Asn Tyr Pro
            20                  25                  30 gcg aaa tct gct ggc tat aat cag ggt gac tgg gtc gct agc ttc aat     144
Ala Lys Ser Ala Gly Tyr Asn Gln Gly Asp Trp Val Ala Ser Phe Asn
        35                  40                  45 ttt tct aag gtc tat gtg ggt gag gag ctt ggc gat cta aat gtt gga     192
Phe Ser Lys Val Tyr Val Gly Glu Glu Leu Gly Asp Leu Asn Val Gly
    50                  55                  60 ggg ggg gct ttg cca aat gct gat gta agt att ggt aat gat aca aca     240
Gly Gly Ala Leu Pro Asn Ala Asp Val Ser Ile Gly Asn Asp Thr Thr
65                  70                  75                  80 ctt acg ttt gat atc gcc tat ttt gtt agc tca aat ata gcg gtg gat     288
Leu Thr Phe Asp Ile Ala Tyr Phe Val Ser Ser Asn Ile Ala Val Asp
                85                  90                  95 ttt ttt gtt ggg gtg cca gct agg gct aaa ttt caa ggt gag aaa tca     336
Phe Phe Val Gly Val Pro Ala Arg Ala Lys Phe Gln Gly Glu Lys Ser
            100                 105                 110 atc tcc tcg ctg gga aga gtc agt gaa gtt gat tac ggc cct gca att     384
Ile Ser Ser Leu Gly Arg Val Ser Glu Val Asp Tyr Gly Pro Ala Ile
        115                 120                 125 ctt tcg ctt caa tat cat tac gat agc ttt gag cga ctt tat cca tat     432
Leu Ser Leu Gln Tyr His Tyr Asp Ser Phe Glu Arg Leu Tyr Pro Tyr
    130                 135                 140 gtt ggg gtt ggt gtt ggt cgg gtg cta ttt ttt gat aaa acc gac ggt     480
Val Gly Val Gly Val Gly Arg Val Leu Phe Phe Asp Lys Thr Asp Gly
145                 150                 155                 160 gct ttg agt tcg ttt gat att aag gat aaa tgg gcg cct gct ttt cag     528
Ala Leu Ser Ser Phe Asp Ile Lys Asp Lys Trp Ala Pro Ala Phe Gln
                165                 170                 175 gtt ggc ctt aga tat gac ctt ggt aac tca tgg atg cta aat tca gat     576
Val Gly Leu Arg Tyr Asp Leu Gly Asn Ser Trp Met Leu Asn Ser Asp
            180                 185                 190 gtg cgt tat att cct ttc aaa acg gac gtc aca ggt act ctt ggc ccg     624
Val Arg Tyr Ile Pro Phe Lys Thr Asp Val Thr Gly Thr Leu Gly Pro
        195                 200                 205 gtt cct gtt tct act aaa att gag gtt gat cct ttc att ctc agt ctt     672
Val Pro Val Ser Thr Lys Ile Glu Val Asp Pro Phe Ile Leu Ser Leu
    210                 215                 220 ggt gcg tca tat gtt ttc taa                                         693
Gly Ala Ser Tyr Val Phe
225                 230
```

<210> SEQ ID NO 2
<211> LENGTH: 230

-continued

<212> TYPE: PRT
<213> ORGANISM: Pseudomonas putida

<400> SEQUENCE: 2

Met Ser Phe Ser Asn Tyr Lys Val Ile Ala Met Pro Val Leu Val Ala
1               5                   10                  15

Asn Phe Val Leu Gly Ala Ala Thr Ala Trp Ala Asn Glu Asn Tyr Pro
            20                  25                  30

Ala Lys Ser Ala Gly Tyr Asn Gln Gly Asp Trp Val Ala Ser Phe Asn
        35                  40                  45

Phe Ser Lys Val Tyr Val Gly Glu Glu Leu Gly Asp Leu Asn Val Gly
    50                  55                  60

Gly Gly Ala Leu Pro Asn Ala Asp Val Ser Ile Gly Asn Asp Thr Thr
65                  70                  75                  80

Leu Thr Phe Asp Ile Ala Tyr Phe Val Ser Ser Asn Ile Ala Val Asp
                85                  90                  95

Phe Phe Val Gly Val Pro Ala Arg Ala Lys Phe Gln Gly Glu Lys Ser
            100                 105                 110

Ile Ser Ser Leu Gly Arg Val Ser Glu Val Asp Tyr Gly Pro Ala Ile
        115                 120                 125

Leu Ser Leu Gln Tyr His Tyr Asp Ser Phe Glu Arg Leu Tyr Pro Tyr
    130                 135                 140

Val Gly Val Gly Val Gly Arg Val Leu Phe Phe Asp Lys Thr Asp Gly
145                 150                 155                 160

Ala Leu Ser Ser Phe Asp Ile Lys Asp Lys Trp Ala Pro Ala Phe Gln
                165                 170                 175

Val Gly Leu Arg Tyr Asp Leu Gly Asn Ser Trp Met Leu Asn Ser Asp
            180                 185                 190

Val Arg Tyr Ile Pro Phe Lys Thr Asp Val Thr Gly Thr Leu Gly Pro
        195                 200                 205

Val Pro Val Ser Thr Lys Ile Glu Val Asp Pro Phe Ile Leu Ser Leu
    210                 215                 220

Gly Ala Ser Tyr Val Phe
225                 230

<210> SEQ ID NO 3
<211> LENGTH: 693
<212> TYPE: DNA
<213> ORGANISM: Pseudomonas putida
<220> FEATURE:
<221> NAME/KEY: AlkL
<222> LOCATION: (1)..(693)
<220> FEATURE:
<221> NAME/KEY: CDS
<222> LOCATION: (1)..(693)

<400> SEQUENCE: 3 atg aat ccg cct att tta aaa aaa ctc gct atg tcg ata tta gca act      48
Met Asn Pro Pro Ile Leu Lys Lys Leu Ala Met Ser Ile Leu Ala Thr
1               5                   10                  15 agt ttt gtg ttg ggt ggg gcc agt gcg tgg tca ggt gaa atc tat tcg      96
Ser Phe Val Leu Gly Gly Ala Ser Ala Trp Ser Gly Glu Ile Tyr Ser
            20                  25                  30 act gaa act gct ggc tac aat cag ggc gac tgg gtt gct agc ttt aat    144
Thr Glu Thr Ala Gly Tyr Asn Gln Gly Asp Trp Val Ala Ser Phe Asn
        35                  40                  45 atg tct aaa gtt tat gta gac gag acg cta ggc tcc cta aat gta ggt    192
Met Ser Lys Val Tyr Val Asp Glu Thr Leu Gly Ser Leu Asn Val Gly
    50                  55                  60

```
ggg gct act gta ccc aat gct gct gta agc atc ggt aat gat aca aca    240
Gly Ala Thr Val Pro Asn Ala Ala Val Ser Ile Gly Asn Asp Thr Thr
 65                  70                  75                  80 gtt tct ttt gat att tcc tat ttt att agt aac aat gta gct ttg gat    288
Val Ser Phe Asp Ile Ser Tyr Phe Ile Ser Asn Asn Val Ala Leu Asp
                 85                  90                  95 ttt ttc gtc ggg att cca gct aaa gct aag ttt caa ggt gaa aaa tcc    336
Phe Phe Val Gly Ile Pro Ala Lys Ala Lys Phe Gln Gly Glu Lys Ser
            100                 105                 110 atc tct gcg ctg gga aga gtc agt gaa gtt gat tat ggc cct gca att    384
Ile Ser Ala Leu Gly Arg Val Ser Glu Val Asp Tyr Gly Pro Ala Ile
        115                 120                 125 ttg tca ctt cag tat cat ttt gat aat ttt gag cga ctt tat cca tat    432
Leu Ser Leu Gln Tyr His Phe Asp Asn Phe Glu Arg Leu Tyr Pro Tyr
130                 135                 140 gtc gga cta ggt gtc ggt cga gtg ttt ttc ttc gac aaa act gat ggt    480
Val Gly Leu Gly Val Gly Arg Val Phe Phe Phe Asp Lys Thr Asp Gly
145                 150                 155                 160 gcc ttg act tca ttt gat atc aaa gat aaa tgg gcg cct gct gtt cag    528
Ala Leu Thr Ser Phe Asp Ile Lys Asp Lys Trp Ala Pro Ala Val Gln
                165                 170                 175 gtc ggc ctt aga tat gat ttt ggt aac tca tgg atg tta aat tca gat    576
Val Gly Leu Arg Tyr Asp Phe Gly Asn Ser Trp Met Leu Asn Ser Asp
            180                 185                 190 gtg cgc tat att cct ttc aaa aca gat gtt tct ggt aca ctt ggg gct    624
Val Arg Tyr Ile Pro Phe Lys Thr Asp Val Ser Gly Thr Leu Gly Ala
        195                 200                 205 gca cct gtt tct acc aag att gag att gat cct ttc att ctg agt ctt    672
Ala Pro Val Ser Thr Lys Ile Glu Ile Asp Pro Phe Ile Leu Ser Leu
210                 215                 220 gga gca tca tat aag ttc tga                                        693
Gly Ala Ser Tyr Lys Phe
225                 230

<210> SEQ ID NO 4
<211> LENGTH: 230
<212> TYPE: PRT
<213> ORGANISM: Pseudomonas putida

<400> SEQUENCE: 4

Met Asn Pro Pro Ile Leu Lys Lys Leu Ala Met Ser Ile Leu Ala Thr
 1               5                  10                  15

Ser Phe Val Leu Gly Gly Ala Ser Ala Trp Ser Gly Glu Ile Tyr Ser
                20                  25                  30

Thr Glu Thr Ala Gly Tyr Asn Gln Gly Asp Trp Val Ala Ser Phe Asn
            35                  40                  45

Met Ser Lys Val Tyr Val Asp Glu Thr Leu Gly Ser Leu Asn Val Gly
50                  55                  60

Gly Ala Thr Val Pro Asn Ala Ala Val Ser Ile Gly Asn Asp Thr Thr
65                  70                  75                  80

Val Ser Phe Asp Ile Ser Tyr Phe Ile Ser Asn Asn Val Ala Leu Asp
                85                  90                  95

Phe Phe Val Gly Ile Pro Ala Lys Ala Lys Phe Gln Gly Glu Lys Ser
            100                 105                 110

Ile Ser Ala Leu Gly Arg Val Ser Glu Val Asp Tyr Gly Pro Ala Ile
        115                 120                 125

Leu Ser Leu Gln Tyr His Phe Asp Asn Phe Glu Arg Leu Tyr Pro Tyr
130                 135                 140
```

Val Gly Leu Gly Val Gly Arg Val Phe Phe Phe Asp Lys Thr Asp Gly
145                 150                 155                 160

Ala Leu Thr Ser Phe Asp Ile Lys Asp Lys Trp Ala Pro Ala Val Gln
                165                 170                 175

Val Gly Leu Arg Tyr Asp Phe Gly Asn Ser Trp Met Leu Asn Ser Asp
            180                 185                 190

Val Arg Tyr Ile Pro Phe Lys Thr Asp Val Ser Gly Thr Leu Gly Ala
        195                 200                 205

Ala Pro Val Ser Thr Lys Ile Glu Ile Asp Pro Phe Ile Leu Ser Leu
    210                 215                 220

Gly Ala Ser Tyr Lys Phe
225                 230

<210> SEQ ID NO 5
<211> LENGTH: 11539
<212> TYPE: DNA
<213> ORGANISM: Artificial
<220> FEATURE:
<223> OTHER INFORMATION: Vector

<400> SEQUENCE: 5

| | | | | |
|---|---|---|---|---|
| gaaaaccgcc | actgcgccgt | taccaccgct | gcgttcggtc | aaggttctgg | accagttgcg | 60 |
| tgagcgcata | cgctacttgc | attacagttt | acgaaccgaa | caggcttatg | tcaattcgcc | 120 |
| tctcaggcgc | cgctggtgcc | gctggttgga | cgccaagggt | gaatccgcct | cgatacccctg | 180 |
| attactcgct | tcctgcgccc | tctcaggcgg | cgatagggga | ctggtaaaac | ggggattgcc | 240 |
| cagacgcctc | ccccgcccct | tcaggggcac | aaatgcggcc | caacggggc | cacgtagtgg | 300 |
| tgcgtttttt | gcgtttccac | ccttttcttc | cttttccctt | taaacctttt | taggacgtct | 360 |
| acaggccacg | taatccgtgg | cctgtagagt | ttaaaaaggg | acggatttgt | tgccattaag | 420 |
| ggacggatttt | gttgttaaga | agggacggat | ttgttgttgt | aaagggacgg | atttgttgta | 480 |
| ttgtgggacg | cagatacagt | gtccccttat | acacaaggaa | tgtcgaacgt | ggcctcaccc | 540 |
| ccaatggttt | acaaaagcaa | tgccctggtc | gaggccgcgt | atcgcctcag | tgttcaggaa | 600 |
| cagcggatcg | ttctggcctg | tattagccag | gtgaagagga | gcgagcctgt | caccgatgaa | 660 |
| gtgatgtatt | cagtgacggc | ggaggacata | gcgacgatgg | cgggtgtccc | tatcgaatct | 720 |
| tcctacaacc | agctcaaaga | agcggccctg | cgcctgaaac | ggcgggaagt | ccggttaacc | 780 |
| caagagccca | atggcaaggg | gaaaagaccg | agtgtgatga | ttaccggctg | ggtgcaaaca | 840 |
| atcatctacc | gggagggtga | gggccgtgta | gaactcaggt | tcaccaaaga | catgctgccg | 900 |
| tacctgacgg | aactcaccaa | acagttcacc | aaatacgcct | ggctgacgt | ggccaagatg | 960 |
| gacagcaccc | acgcgatcag | gctttacgag | ctgctcatgc | aatgggacag | catcggccag | 1020 |
| cgcgaaatag | aaattgacca | gctgcgaaag | tggtttcaac | tggaaggccg | gtatccctcg | 1080 |
| atcaaggact | tcaagttgcg | agtgcttgat | ccagccgtga | cgcagatcaa | cgagcacagc | 1140 |
| ccgctacagg | tggagtgggc | gcagcgaaag | accggcgca | aggtcacaca | tctgttgttc | 1200 |
| agttttggac | cgaagaagcc | cgccaaggcg | gtgggtaagg | cccagcgaa | gcgcaaggcc | 1260 |
| gggaagattt | cagatgctga | gatcgcgaaa | caggctcgcc | ctggtgagac | atgggaagcg | 1320 |
| gcccgcgctc | gactaaccca | gatgccgctg | gatctggcct | agaggccgtg | gccaccacgg | 1380 |
| cccggcctgc | ctttcaggct | gcattattga | agcatttatc | agggttattg | tctcatgagc | 1440 |
| ggatacatat | ttgaatgtat | ttagaaaaat | aaacaaaaga | gtttgtagaa | acgcaaaaag | 1500 |

```
gccatccgtc aggatggcct tctgcttaat ttgatgcctg cagtttatg gcgggcgtcc    1560 tgcccgccac cctccgggcc gttgcttcgc aacgttcaaa tccgctcccg gcggatttgt    1620
cctactcagg agagcgttca ccgacaaaca acagataaaa cgaaaggccc agtctttcga    1680
ctgagccttt cgttttattt gatgcctggc agttccctac tctcgcatgg ggagacccca    1740
cactaccatc ggcgctacgg cgtttcactt ctgagttcgg catgggtca ggtgggacca    1800 ccgcgctact gccgccaggc aaattctgtt ttatcagacc gcttctgcgt tctgatttaa    1860
tctgtatcag gctgaaaatc ttctctcatc cgccaaaaca gaagcttggc tgcaggtcga    1920
caagcgctga atgggtatcg gcactagagt ttaacttggc taggctaatt ggtatggtca    1980
tttttatttt gtcctgaatt acctagaatg acttgaagtt ttaatcttca cttttcctcg    2040
tagagcacat agtcttcttt cgtagccccg caatccggac agcaccagtc atcaggaata    2100
tcctcaaagc gagtacctgg agtaaaaccc tcggcctcat cgcccaacgc tcatcatat    2160 atatggccac aagtaataca tatccacttc aagtatgctt tccgccttg gcatcagac    2220 cttggaggtt gagttttata tagatcttgg cctttaacgt cggcactagg caatttctct    2280
aagcttgtcg gcgcaaccac tgcttcagca gttaaacttg tgccactaac ctcggataaa    2340
tttggcgaag tatgggttga ggtgacgccc ttttcaccta cgccgctctc aattaacatg    2400
aagtcaagct tgtctcgaac ggcgcaatcg gggcagcacc aatcctcagg ataaggtgc    2460 caaggcgtac ctggagaaaa cccctcatgc acattacccg cactctcatc ataaacataa    2520
ttacaatccg ggcatttata gctagccata ctcatcacca tgtcaaattg ttattttgcg    2580
ttgcggcaaa tttgcgttat ttatttctca tcttcttcct tgtggaagat tttcttacaa    2640
cctgtggggt gctcgcctga tcaagaactt cagtcttagc cgcacagccc tcatttttat    2700
tttcttgatt aagtgggatc actaattctg cggccaaaac tgccattcca gttggagtag    2760
catctgaaat accactttcc gagttggcaa gctgactatt caccctagc tgtgtttctt    2820 tcgagggaga atccgcgaga aagataaagt ccaccttgtc tcgaactgcg cagtccgggc    2880
atgcccaatc tttggggata tcattccagc tggtgttcgg gtggaaacct tcgtgcggct    2940 ccccccttatt ttcatcatag atatactgac aatctggaca ctggtacctt gacattctcc    3000
cactctccta ttaactcagc gttagtcgct gctccgacaa cttcatcaga gtgtaactat    3060
cggagcaggt cgccttcaaa gcaattacag agaggcaatc aaccctcagc actttagcga    3120
agtgcactct ttgtgagagc tttcaacgcc gcacataaaa ttgaagcact tattgtaaat    3180
atcgaccgcc gggctctgcg tgctcacata actacgatgc taccgcagag gtactcgaac    3240
tatgaccagc actactagtg ccaaattttt tcaaataggt ttctcgcatc gaatcatcaa    3300
tttggatctt attaaggtca ccaccagccc aatctactac cttgggatcc ataactgatc    3360
taaaccactg aggaatcatc gccatcaaaa atgcaccagg gtaacccgtc ggaagagccg    3420
gcaggccggg aaaatcccga agtgactgat aagaacgtgt tggatgcgcg tggtgatccg    3480
agtgccgctg aaggtggaac agcactagat tagagacgat gtgattacta ttccaagaat    3540
ggtgcggctt ttgatgctca tatcgaccgt cctccatttt ttgacggagc aagccgtaat    3600
gttcaatata gttcgcactg gtcagctgcc accaaccgaa agccatttga atcggcagga    3660
acaccagcat cttaggtcca aacaaggcaa ggagaacggc gtaaagaata actgtgatga    3720
tcattggttg gaggatttca ttatcgaaac tccaaacgct ttggccacgg cgcgaaaggc    3780
gttgttcctc aagcccccaa gcacgaataa atgctcctgg gatctcacgg attgaaaact    3840
tataaatgct ttctcccatc cgggatgttg caggatccat cggtgtagcg acatcacggt    3900
```

```
gatgacccct attatgctca ataaagaagt gaccgtaccc tacgacagcc aacacaattt   3960
tggccatcca acgatcaaaa gtctccttct tgtgaccgag ttcgtgtcct gtattgagcg   4020
ctagtccgtt cacgataccc agtgacaagg caagcgcacc aatttcaagc caagacattg   4080
gctgagttcc gacccaccat gctgacacaa ttaatgcagc gtaatgcata ggaactgtta   4140
gatatgtcaa aactcgatag taccgctcct tctctagttt cggcaccact tcttcaggcg   4200
gattattaaa gtcctcacca aacatcgcat caagcaatgg aagtgcgccg taccatacga   4260
gcaataccag cccataaaaa atcccccaac cagtttcatt tgcaagccag attccgatca   4320
tcggagtagc cggccacaaa gttgatagta tccagagata tttcttttta tctacgtact   4380
ctggagcgga atccagaact ctgtgtttct caagcatatg gaattctcca atttttatta   4440
aattagtcgc tacgagattt aagacgtaat tttatgccta actgagaaag ttaagccgcc   4500
cactctcact ctcgacatct taaacctgag ctaatcggac gcttgcgcca actacaccta   4560
cgggtagttt ttgctccgtc gtctgctgga aaaacgagc ctggccgcaa gcatgccagg   4620
taccgcgagc tactcgcgac ggctgaaagc accgaaatga gcgagctatc tggtcgattt   4680
tgacccggtg cccgtcttca aaatcggcga aggccgaagt cggccagaaa tagcggccta   4740
cttcagacct tccctagtaa atattttgca ccaccgatca tgccgactac acttaagtgt   4800
agttttaata tttaacaccg taacctatgg tgaaaatttc cagtcagctg gcgcgagaat   4860
agcataatga aaataataat aaataatgat ttcccggtcg ctaaggtcgg agcggatcaa   4920
attacgactc tagtaagtgc caaagttcat agttgcatat atcggccaag attgagtatc   4980
gcggatggag ccgctcccag agtatgcctt tacagagccc cacctggata tgggaaaacc   5040
gttgctcttg cgttcgagtg gctacgccac agaacagccg gacgtcctgc agtgtggctt   5100
tctttaagag ccagttctta cagtgaattt gatatctgcg cagagattat tgagcagctt   5160
gaaactttcg aaatggtaaa attcagccgt gtgagagagg gtgtgagcaa gcctgcgctc   5220
ttgcgagacc ttgcatctag tctttggcag agcacctcga ataacgagat agaaacgcta   5280
gtttgtttgg ataatattaa tcatgactta gacttgccgt tgttcacgc acttatggag   5340 tttatgttaa atacaccaaa aaatatcagg tttgcagttg caggcaatac aataaaaggg   5400
ttctcgcagc ttaaacttgc aggcgctatg cgggagtaca ccgagaaaga cttggccttt   5460
agcgcagaag aggcggtggc gttagcgag cagagtctg ttcttggagt tcctgaagaa   5520
cagatagaga ccttggtgca agaagttgag gggtggcctg ctcttgtagt ttttttgtta   5580
aagcgtgagt tgccggccaa gcatatttca gcagtagttg aagtagacaa ttactttagg   5640
gatgaaatat ttgaggcgat tcccgagcgc tatcgtgttt ttcttgcaaa ttcttcattg   5700
ctcgatttcg tgacgcctga tcaatacaat tatgtattca aatgcgtcaa tggggtctca   5760
tgtattaagt atttaagcac taattacatg ttgcttcgcc atgtgagcgg tgagccagcg   5820
cagtttacac tgcatccagt actgcgtaat tttctacgag aaattacttg gactgaaaat   5880
cctgctaaaa gatcctacct gcttaagcgt gcagctttct ggcattggcg tagaggtgaa   5940
taccagtatg caatacgaat atccctacgg gcgaatgact gtcgctgggc agtcagcatg   6000
tctgagagaa taattttaga tttgtcattt cgtcagggcg aaatagatgc gctgagacag   6060
tggctgttag agctgccgaa gcaggcctgg caccaaaaac ccatagtgct tattagttac   6120
gcgtgggtat tgtatttcag tcagcaaggc gcgcagcag agaagttaat taagagccta   6180
tcttcacaat ccgataaaaa aaataaatgg caagaaaagg aatggctgca gcttgtgctt   6240
```

```
gcaataggta aagcaaccaa agatgaaatg ctttcgagtg aggagctctg taataagtgg   6300
attagtttat ttggggattc aaacgcagtt ggaaaagggg ccgcgctaac ctgtttggct   6360
tttattttg ccagtgagta tagatttgca gagttggaga aggtgctggc tcaggcccaa   6420
gccgtgaata aatttgcaaa acaaaatttt gcttttggtt ggctgtatgt cgcgaggttt   6480
caacaagccc tagcaagcgg aaaaatgggc tgggcgaggc agattataac tcaagcacgc   6540
acagacagtc gcgcgcagat gatggaatcc gagtttactt cgaaaatgtt tgacgctcta   6600
gagcttgagt tacattatga attgcgctgc ttggacacct cagaagaaaa gctctccaaa   6660
attttagagt tcatttccaa tcacggggtg acagacgtgt ttttttccgt atgccgtgct   6720
gtgtcagctt ggcggcttgg aaggagtgac ctaaatggct ccattgagat attggagtgg   6780
gcgaaggcgc atgcggttga aaaaaatcta ccaagattgg aagttatgag ccaaattgag   6840
atctatcagc gcttagtctg tcaaggcata acgggcataa ataatttaaa aactcttgaa   6900
gatcataaga ttttctccgg acagcactca gccccctaa aagcacgcct gctgcttgtt   6960
caatcactag tgctttcccg agatcggaac tttcatagtg ccgcgcacag agcgttattg   7020
gctattcagc aagcccgtaa aattaacgcg ggccagctgg aagtccgtgg attattgtgt   7080
ttggccggag cgcaggcagg tgccggtgat ttaaaaaagg ctcagcttaa cattgtttat   7140
gcagtggaga tagcaaaaca gcttcaatgc tttcaaacag ttcttgatga agtatgttta   7200
attgagcgaa taataccggc ttcatgtgaa gccttcacag cagttaattt agatcaagcg   7260
attgggggctt ttagtcttcc gcgaatagtt gagattggaa agtccgcaga gaataaagct   7320
gacgctttat tgcacggaa gcagattgct gtcttgaggc ttgtaaaaga ggggtgctca   7380
aacaaacaaa tagcaacaaa tatgcatgtc accgaagatg ctataaagtg gcatatgagg   7440
aaaatatttg ccaccttgaa tgtagtgaat cgcacgcaag caacaattga agctgagcgt   7500
caaggaatta tctaaaataa tcggcattaa gtgatatagt gaaagtata ccggagagag   7560
aattatggca atcgttgttg ttggcgctgg tacagctgga gtaaatgctg cgttctggct   7620
tcgtcaatat ggttataaag gggaaattag gattttagc agggagtctg tggcgcctta   7680
tcagcggcct cctctatcca aggcttttct gacaagtgag attgcagaat ccgcagtgcc   7740
attaaagcca gaaggttttt atacgaataa caatattacc atttcgttaa atacaccgat   7800
tgtatcaatc gacgtggggc gtaagatagt ttcttctaaa gatggaaag aatacgcgta   7860
tgaaaaattg attcttgcaa cacctgctag cgcacgtagg ttaacctgcg aggggtctga   7920
actgtctggg gtctgctatt tacgcagtat ggaagacgcc aaaaatttac gtaggaaact   7980
tgtggagagt gcgtctgttg ttgtgttggg cggcggagta atcgggcttg aagtcgcctc   8040
agctgcggtg ggcttaggga agagggtcac agtgatagaa gccacccgcc gtgtaatggc   8100
gcgcgtggtt acgccggcag cagcaaactt agtcagagcc cgcctggagg ctgaaggaat   8160
tgagttcaag ctgaatgcga aattaacgtc tataaagggc aggaatggcc atgttgaaca   8220
atgcgtactt gaaagtggag aagaaattca ggcggatctg attgtagttg aatcggtgc   8280
tatcccagag ctagagctgg caactgaggc ggcccttgaa gtgagtaatg tgttgtggt   8340
cgatgatcag atgtgtacat cggatacaag tatatatgca atcggcgact cgcaatggc   8400
tagaaatcct tttggggaa cgatggtacg tttagagaca attcataatg cggttacaca   8460
cgctcaaatt gtcgcaagta gcatctgtgg cacatcaaca ccagcaccaa ccccaccacg   8520
gttctggtct gatcttaaag ggatggcgct gcaaggactt ggtgctctaa aggactacga   8580
taaactcgtt gttgcaatta ataacgaaac tcttgaacta gaagtccttg cgtacaagca   8640
```

```
ggagcgactg attgcaactg agacaataaa tttgcctaaa cgtcaaggtg cgcttgcagg    8700
gagtataaaa ttacctgatt agcaatgatg ctcagccact cgaaccaacg gtcgcgatag    8760
ggacggcagt tacctgccgc cccccgcact ccgtacgtgc ggaactaccg cgtaaaatgt    8820
ggcccaggct gttatgtggc gcttgggcgg ggaagtattg ccatatttgg tgatgaccgt    8880
tttctacgcc acataaatcg gtggtggcta tggtgggatt tcccttgctg aaatgggaga    8940
tccgatcatg ttcgagctct tattcaaata cactgctgtg ttggcggtaa gcgttctcga    9000
gctcatagtc cacgacgccc gtgattttgt agccctggcc gacggccagc aggtaggccg    9060
acaggctcat gccggccgcc gccgccttt cctcaatcgc tcttcgttcg tctggaaggc    9120
agtacacctt gataggtggg ctgcccttcc tggttggctt ggtttcatca gccatccgct    9180
tgccctcatc tgttacgccg gcggtagccg gccagcctcg cagagcagga ttcccgttga    9240
gcaccgccag gtgcgaataa gggacagtga agaaggaaca cccgctcgcg ggtgggccta    9300
cttcacctat cctgcccggc tgacgccgtt ggatacacca aggaaagtct acacgaaccc    9360
tttggcaaaa tcctgtatat cgtgcgaaaa aggatggata taccgaaaaa atcgctataa    9420
tgaccccgaa gcagggttat gcagcggaaa agcgctgctt ccctgctgtt ttgtggaata    9480
tctaccgact ggaaacaggc aaatgcagga aattactgaa ctgaggggac aggcgagaga    9540
ggatcaatgg ctatctgggg gaccgagggc tgtcgctgcg ccaaggcacg attggagatc    9600
ccctatgcgg tgtgaaatac cgcacagatg cgtaaggaga aaataccgca tcaggcgctc    9660
ttccgcttcc tcgctcactg actcgctgcg ctcggtcgtt cggctgcggc gagcggtatc    9720
agctcactca aaggcggtaa tacggttatc cacagaatca ggggataacg caggaaagaa    9780
catgtgagca aaaggccagc aaaaggccag gaaccgtaaa aaggccgcgt tgctggcgtt    9840
tttccatagg ctccgccccc ctgacgagca tcacaaaaat cgacgctcaa gtcagaggtg    9900
gcgaaacccg acaggactat aaagatacca ggcgtttccc cctggaagct ccctcgtgcg    9960
ctctcctgtt ccgaccctgc cgcttaccgg atacctgtcc gcctttctcc cttcgggaag    10020
cgtggcgctt tctcatagct cacgctgtag gtatctcagt tcggtgtagg tcgttcgctc    10080
caagctgggc tgtgtgcacg aaccccccgt tcagcccgac cgctgcgcct tatccggtaa    10140
ctatcgtctt gagtccaacc cggtaagaca cgacttatcg ccactggcag cagccactgg    10200
taacaggatt agcagagcga ggtatgtagg cggtgctaca gagttcttga agtggtggcc    10260
taactacggc tacactagaa ggacagtatt tggtatctgc gctctgctga agccagttac    10320
cttcggaaaa agagttggta gctcttgatc cggcaaacaa accaccgctg gtagcggtgg    10380
tttttttgtt tgcaagcagc agattacgcg cagaaaaaaa ggatctcaag aagatccttt    10440
gatcttttct acgggtctg acgctcagtg gaacgaaaac tcacgttaag ggattttggt    10500
catgagatta tcaaaaagga tcttcaccta gatccttta aattaaaaat gaagttttaa    10560
atcaatctaa agtatatatg agtaaacttg gtctgacagt taccaatcga ttggtcggtc    10620
atttcgaacc ccagagtccc gctcagaaga actcgtcaag aaggcgatag aaggcgatgc    10680
gctgcgaatc gggagcggcg ataccgtaaa gcacgaggaa gcggtcagcc cattcgccgc    10740
caagctcttc agcaatatca cgggtagcca acgctatgtc ctgatagcgg tccgccacac    10800
ccagccggcc acagtcgatg aatccagaaa agcggccatt ttccaccatg atattcggca    10860
agcaggcatc gccatgggtc acgacagat cctcgccgtc gggcatgcgc gccttgagcc    10920
tggcgaacag ttcggctggc gcgagcccct gatgctcttc gtccagatca tcctgatcga    10980
```

| | |
|---|---:|
| caagaccggc ttccatccga gtacgtgctc gctcgatgcg atgtttcgct tggtggtcga | 11040 |
| atgggcaggt agccggatca agcgtatgca gccgccgcat tgcatcagcc atgatggata | 11100 |
| ctttctcggc aggagcaagg tgagatgaca ggagatcctg ccccggcact tcgcccaata | 11160 |
| gcagccagtc ccttcccgct tcagtgacaa cgtcgagcac agctgcgcaa ggaacgcccg | 11220 |
| tcgtggccag ccacgatagc cgcgctgcct cgtcctgcag ttcattcagg gcaccggaca | 11280 |
| ggtcggtctt gacaaaaaga accgggcgcc cctgcgctga cagccggaac acggcggcat | 11340 |
| cagagcagcc gattgtctgt tgtgcccagt catagccgaa tagcctctcc acccaagcgg | 11400 |
| ccggagaacc tgcgtgcaat ccatcttgtt caatcatgcg aaacgatcct catcctgtct | 11460 |
| cttgatcaga tcttgatccc ctgcgccatc agatccttgg cggcaagaaa gccatccagt | 11520 |
| ttactttgca gggcttccc | 11539 |

<210> SEQ ID NO 6
<211> LENGTH: 36
<212> TYPE: DNA
<213> ORGANISM: Artificial
<220> FEATURE:
<223> OTHER INFORMATION: Primer

<400> SEQUENCE: 6

| | |
|---|---:|
| acgcgtcgac ctgtaacgac aacaaaacga gggtag | 36 |

<210> SEQ ID NO 7
<211> LENGTH: 30
<212> TYPE: DNA
<213> ORGANISM: Artificial
<220> FEATURE:
<223> OTHER INFORMATION: Primer

<400> SEQUENCE: 7

| | |
|---|---:|
| acgcgtcgac ctgcgacagt gacagacctg | 30 |

<210> SEQ ID NO 8
<211> LENGTH: 12348
<212> TYPE: DNA
<213> ORGANISM: Artificial
<220> FEATURE:
<223> OTHER INFORMATION: Vector

<400> SEQUENCE: 8

| | |
|---|---:|
| atcgattgga tgcccgaggc atagactgta caaaaaaaca gtcataacaa gccatgaaaa | 60 |
| ccgccactgc gccgttacca ccgctgcgtt cggtcaaggt tctggaccag ttgcgtgagc | 120 |
| gcatacgcta cttgcattac agtttacgaa ccgaacaggc ttatgtcaat cgcctctca | 180 |
| ggcgccgctg gtgccgctgg ttggacgcca agggtgaatc cgcctcgata ccctgattac | 240 |
| tcgcttcctg cgccctctca ggcggcgata ggggactggt aaaacgggga ttgcccagac | 300 |
| gcctcccccg ccccttcagg ggcacaaatg cggcccaac ggggcacgt agtggtgcgt | 360 |
| tttttgcgtt tccaccctt tcttcctttt cccttttaaa cctttaggga cgtctacagg | 420 |
| ccacgtaatc cgtggcctgt agagtttaaa aagggacgga tttgttgcca ttaagggacg | 480 |
| gatttgttgt taagaaggga cggatttgtt gttgtaaagg acggatttg ttgtattgtg | 540 |
| ggacgcagat acagtgtccc cttatacaca aggaatgtcg aacgtggcct caccccaat | 600 |
| ggtttacaaa agcaatgccc tggtcgaggc cgcgtatcgc ctcagtgttc aggaacagcg | 660 |
| gatcgttctg gcctgtatta gccaggtgaa gaggagcgag cctgtcaccg atgaagtgat | 720 |
| gtattcagtg acggcggagg acatagcgac gatggcgggt gtccctatcg aatcttccta | 780 |

```
caaccagctc aaagaagcgg ccctgcgcct gaaacggcgg gaagtccggt taacccaaga      840
gcccaatggc aagggggaaaa gaccgagtgt gatgattacc ggctgggtgc aaacaatcat     900
ctaccgggag ggtgagggcc gtgtagaact caggttcacc aaagacatgc tgccgtacct      960
gacggaactc accaaacagt tcaccaaata cgccttggct gacgtggcca agatggacag     1020
cacccacgcg atcaggcttt acgagctgct catgcaatgg acagcatcg gccagcgcga     1080 aatagaaatt gaccagctgc gaaagtggtt tcaactggaa ggccggtatc cctcgatcaa    1140
ggacttcaag ttgcgagtgc ttgatccagc cgtgacgcag atcaacgagc acagcccgct    1200
acaggtggag tgggcgcagc gaaagaccgg gcgcaaggtc acacatctgt tgttcagttt    1260
tggaccgaag aagcccgcca aggcggtggg taaggcccca gcgaagcgca aggccgggaa    1320
gatttcagat gctgagatcg cgaaacaggc tcgccctggt gagacatggg aagcggcccg    1380
cgctcgacta acccagatgc cgctggatct ggcctagagg ccgtggccac cacggcccgg    1440
cctgcctttc aggctgcatt attgaagcat ttatcagggt tattgtctca tgagcggata    1500
catatttgaa tgtatttaga aaaataaaca aaagagtttg tagaaacgca aaaaggccat    1560
ccgtcaggat ggccttctgc ttaatttgat gcctggcagt ttatggcggg cgtcctgccc    1620
gccaccctcc gggccgttgc ttcgcaacgt tcaaatccgc tcccggcgga tttgtcctac    1680
tcaggagagc gttcaccgac aaacaacaga taaaacgaaa ggcccagtct ttcgactgag    1740
cctttcgttt tatttgatgc ctggcagttc cctactctcg catggggaga ccccacacta    1800
ccatcggcgc tacggcgttt cacttctgag ttcggcatgg ggtcaggtgg gaccaccgcg    1860
ctactgccgc caggcaaatt ctgttttatc agaccgcttc tgcgttctga tttaatctgt    1920
atcaggctga aaatcttctc tcatccgcca aacagaagc ttggctgcag gtcgacctgc    1980
gacagtgaca gacctgatta cttagaaaac atatgacgca ccaagactga gaatgaaagg    2040
atcaacctca atttttagtag aaacaggaac cgggccaaga gtacctgtga cgtccgtttt    2100
gaaaggaata taacgcacat ctgaatttag catccatgag ttaccaaggt catatctaag    2160
gccaacctga aaagcaggcg cccatttatc cttaatatca aacgaactca aagcaccgtc    2220
ggttttatca aaaaatagca cccgaccaac accaaccccca acatatggat aaagtcgctc    2280
aaagctatcg taatgatatt gaagcgaaag aattgcaggg ccgtaatcaa cttcactgac    2340
tcttcccagc gaggagattg atttctcacc ttgaaattta gccctagctg caccccaac     2400 aaaaaaatcc accgctatat ttgagctaac aaaataggcg atatcaaacg taagtgttgt    2460
atcattacca atacttacat cagcatttgg caaagccccc cctccaacat ttagatcgcc    2520
aagctcctca cccacataga ccttagaaaa attgaagcta gcgacccagt caccctgatt    2580
atagccagca gatttcgccg gataattttc attcgcccat gcagtggccg cccccaaaac    2640
aaaattagca accaacaccg gcatcgcgat tactttataa ttagaaaaac tcattgtgct    2700
accctcgttt tgttgtcgtt acaggtcgac aagcgctgaa tgggtatcgg cactagagtt    2760
taacttggct aggctaattg gtatggtcat ttttatttg tcctgaatta cctagaatga     2820
cttgaagttt taatcttcac ttttcctcgt agagcacata gtcttctttc gtagcccgc     2880 aatccggaca gcaccagtca tcaggaatat cctcaaagcg agtacctgga gtaaaaccct    2940
cggcctcatc gcccaacgcc tcatcatata tatggccaca agtaatacat atccacttca    3000
agtatgcttt cccgccttgg gcatcagacc ttggaggttg agttttatat agatcttggc    3060 cttttaacgtc ggcactaggc aatttctcta agcttgtcgg cgcaaccact gcttcagcag    3120
```

```
ttaaacttgt gccactaacc tcggataaat ttggcgaagt atgggttgag gtgacgccct   3180
tttcacctac gccgctctca attaacatga agtcaagctt gtctcgaacg gcgcaatcgg   3240
ggcagcacca atcctcagga ataaggtgcc aaggcgtacc tggagaaaac ccctcatgca   3300
cattacccgc actctcatca taaacataat tacaatccgg gcatttatag ctagccatac   3360
tcatcaccat gtcaaattgt tattttgcgt tgcggcaaat ttgcgttatt tatttctcat   3420
cttcttcctt gtggaagatt ttcttacaac ctgtggggtg ctcgcctgat caagaacttc   3480
agtcttagcc gcacagccct catttttatt ttcttgatta gtgggatca ctaattctgc    3540
ggccaaaact gccattccag ttggagtagc atctgaaata ccactttccg agttggcaag   3600
ctgactattc accctagct gtgtttcttt cgagggagaa tccgcgagaa agataaagtc     3660
caccttgtct cgaactgcgc agtccgggca tgcccaatct tggggatat cattccagct    3720
ggtgttcggg tggaaacctt cgtgcggctc ccccttattt tcatcataga tatactgaca   3780
atctggacac tggtaccttg acattctccc actctcctat taactcagcg ttagtcgctg   3840
ctccgacaac ttcatcagag tgtaactatc ggagcaggtc gccttcaaag caattacaga   3900
gaggcaatca accctcagca ctttagcgaa gtgcactctt tgtgagagct ttcaacgccg   3960
cacataaaat tgaagcactt attgtaaata tcgaccgccg ggctctgcgt gctcacataa   4020
ctacgatgct accgcagagg tactcgaact atgaccagca ctactagtgc caaattttt   4080
caaataggtt tctcgcatcg aatcatcaat ttggatctta ttaaggtcac caccagccca   4140
atctactacc ttgggatcca taactgatct aaaccactga ggaatcatcg ccatcaaaaa   4200
tgcaccaggg taacccgtcg gaagagccgg caggccggga aaatcccgaa gtgactgata   4260
agaacgtgtt ggatgcgcgt ggtgatccga gtgccgctga aggtggaaca gcactagatt   4320
agagacgatg tgattactat tccaagaatg gtgcggcttt tgatgctcat atcgaccgtc   4380
ctccattttt tgacggagca agccgtaatg ttcaatatag ttcgcactgg tcagctgcca   4440
ccaaccgaaa gccatttgaa tcggcaggaa caccagcatc ttaggtccaa acaaggcaag   4500
gagaacggcg taaagaataa ctgtgatgat cattggttgg aggatttcat tatcgaaact   4560
ccaaacgctt tggccacggc gcgaaaggcg ttgttcctca agcccccaag cacgaataaa   4620
tgctcctggg atctcacgga ttgaaaactt ataaatgctt tctcccatcc gggatgttgc   4680
aggatccatc ggtgtagcga catcacggtg atgacccta ttatgctcaa taagaagtg     4740
accgtaccct acgacagcca acacaatttt ggccatccaa cgatcaaaag tctccttctt   4800
gtgaccgagt tcgtgtcctg tattgagcgc tagtccgttc acgataccca gtgacaaggc   4860
aagcgcacca atttcaagcc aagacattgg ctgagttccg acccaccatg ctgacacaat   4920
taatgcagcg taatgcatag gaactgttag atatgtcaaa actcgatagt accgctcctt   4980
ctctagtttc ggcaccactt cttcaggcgg attattaaag tcctcaccaa acatcgcatc   5040
aagcaatgga agtgcgccgt accatacgag caataccagc ccataaaaaa tcccccaacc   5100
agtttcattt gcaagccaga ttccgatcat cggagtagcc ggcacaaag ttgatagtat    5160
ccagagatat ttctttttat ctacgtactc tggagcggaa tccagaactc tgtgtttctc   5220
aagcatatgg aattctccaa ttttattaa attagtcgct acgagattta agacgtaatt   5280
ttatgcctaa ctgagaaagt taagccgccc actctcactc tcgacatctt aaacctgagc   5340
taatcggacg cttgcgccaa ctacacctac gggtagtttt tgctccgtcg tctgctggaa   5400
aaacacgagc tggccgcaag catgccaggt accgcgagct actcgcgacg gctgaaagca   5460
ccgaaatgag cgagctatct ggtcgatttt gacccggtgc ccgtcttcaa aatcggcgaa   5520
```

```
ggccgaagtc ggccagaaat agcggcctac ttcagacctt ccctagtaaa tattttgcac    5580
caccgatcat gccgactaca cttaagtgta gttttaatat ttaacaccgt aacctatggt    5640
gaaaatttcc agtcagctgg cgcgagaata gcataatgaa ataataata  aataatgatt    5700 tcccggtcgc taaggtcgga gcggatcaaa ttacgactct agtaagtgcc aaagttcata    5760
gttgcatata tcggccaaga ttgagtatcg cggatggagc cgctcccaga gtatgccttt    5820
acagagcccc acctggatat gggaaaaccg ttgctcttgc gttcgagtgg ctacgccaca    5880
gaacagccgg acgtcctgca gtgtggcttt ctttaagagc cagttcttac agtgaatttg    5940
atatctgcgc agagattatt gagcagcttg aaactttcga atggtaaaa  ttcagccgtg    6000 tgagagaggg tgtgagcaag cctgcgctct tgcgagacct tgcatctagt ctttggcaga    6060
gcacctcgaa taacgagata gaaacgctag tttgtttgga taatattaat catgacttag    6120
acttgccgtt gttgcacgca cttatggagt ttatgttaaa tacaccaaaa aatatcaggt    6180
ttgcagttgc aggcaataca ataaaagggt tctcgcagct taaacttgca ggcgctatgc    6240
gggagtacac cgagaaagac ttggccttta gcgcagaaga ggcggtggcg ttagcggagg    6300
cagagtctgt tcttggagtt cctgaagaac agatagagac cttggtgcaa gaagttgagg    6360
ggtggcctgc tcttgtagtt ttttgttaa  agcgtgagtt gccggccaag catatttcag    6420
cagtagttga agtagacaat tactttaggg atgaaatatt tgaggcgatt cccgagcgct    6480
atcgtgtttt tcttgcaaat tcttcattgc tcgatttcgt gacgcctgat caatacaatt    6540
atgtattcaa atgcgtcaat ggggtctcat gtattaagta tttaagcact aattacatgt    6600
tgcttcgcca tgtgagcggt gagccagcgc agtttacact gcatccagta ctgcgtaatt    6660
ttctacgaga aattacttgg actgaaaatc ctgctaaaag atcctacctg cttaagcgtg    6720
cagctttctg gcattggcgt agaggtgaat accagtatgc aatacgaata tccctacggg    6780
cgaatgactg tcgctgggca gtcagcatgt ctgagagaat aattttagat ttgtcatttc    6840
gtcagggcga aatagatgcg ctgagacagt ggctgttaga gctgccgaag caggcctggc    6900
accaaaaacc catagtgctt attagttacg cgtgggtatt gtatttcagt cagcaaggcg    6960
cgcgagcaga gaagttaatt aaagaccat  cttcacaatc cgataaaaaa aataaatggc    7020
aagaaaagga atggctgcag cttgtgcttg caataggtaa agcaaccaaa gatgaaatgc    7080
tttcgagtga ggagctctgt aataagtgga ttagtttatt tggggattca aacgcagttg    7140 gaaaagggc  cgcgctaacc tgtttggctt ttattttgc  cagtgagtat agatttgcag    7200
agttggagaa ggtgctggct caggcccaag ccgtgaataa atttgcaaaa caaaattttg    7260
cttttggttg gctgtatgtc gcgaggtttc aacaagccct agcaagcgga aaaatgggct    7320
gggcgaggca gattataact caagcacgca cagacagtcg cgcgcagatg atggaatccg    7380 agttacttc  gaaaatgttt gacgctctag agcttgagtt acattatgaa ttgcgctgct    7440
tggacacctc agaagaaaag ctctccaaaa ttttagagtt catttccaat cacggggtga    7500
cagacgtgtt ttttccgta  tgccgtgctg tgtcagcttg gcggcttgga aggagtgacc    7560
taaatggctc cattgagata ttggagtggg cgaaggcgca tgcggttgaa aaaaatctac    7620
caagattgga agtatgagc  caaattgaga tctatcagcg cttagtctgt caaggcataa    7680
cgggcataaa taatttaaaa actcttgaag atcataagat tttctccgga cagcactcag    7740 ccccccctaaa agcacgcctg ctgcttgttc aatcactagt gctttcccga gatcggaact    7800
ttcatagtgc cgcgcacaga gcgttattgg ctattcagca agcccgtaaa attaacgcgg    7860
```

```
gccagctgga agtccgtgga ttattgtgtt tggccggagc gcaggcaggt gccggtgatt   7920
taaaaaaggc tcagcttaac attgtttatg cagtggagat agcaaaacag cttcaatgct   7980
ttcaaacagt tcttgatgaa gtatgtttaa ttgagcgaat aataccggct tcatgtgaag   8040
ccttcacagc agttaattta gatcaagcga ttggggcttt tagtcttccg cgaatagttg   8100
agattggaaa gtccgcagag aataaagctg acgctttatt gacacggaag cagattgctg   8160
tcttgaggct tgtaaaagag gggtgctcaa acaaacaaat agcaacaaat atgcatgtca   8220
ccgaagatgc tataaagtgg catatgagga aaatatttgc caccttgaat gtagtgaatc   8280
gcacgcaagc aacaattgaa gctgagcgtc aaggaattat ctaaaataat cggcattaag   8340
tgatatagtg aaaagtatac cggagagaga attatggcaa tcgttgttgt tggcgctggt   8400
acagctggag taaatgctgc gttctggctt cgtcaatatg gttataaagg gaaattagg   8460 attttttagca gggagtctgt ggcgccttat cagcggcctc ctctatccaa ggcttttctg   8520
acaagtgaga ttgcagaatc cgcagtgcca ttaaagccag aaggttttta tacgaataac   8580
aatattacca tttcgttaaa tacaccgatt gtatcaatcg acgtggggcg taagatagtt   8640
tcttctaaag atggaaaaga atacgcgtat gaaaaattga ttcttgcaac acctgctagc   8700
gcacgtaggt taacctgcga ggggtctgaa ctgtctgggg tctgctattt acgcagtatg   8760
gaagacgcca aaaatttacg taggaaactt gtggagagtg cgtctgttgt tgtgttgggc   8820
ggcggagtaa tcgggcttga agtcgcctca gctgcggtgg gcttagggaa gagggtcaca   8880
gtgatagaag ccaccccgcg tgtaatggcg cgcgtggtta cgccggcagc agcaaactta   8940
gtcagagccc gcctggaggc tgaaggaatt gagttcaagc tgaatgcgaa attaacgtct   9000
ataaagggca ggaatggcca tgttgaacaa tgcgtacttg aaagtggaga gaaaattcag   9060
gcggatctga ttgtagttgg aatcggtgct atcccagagc tagagctggc aactgaggcg   9120
gcccttgaag tgagtaatgg tgttgtggtc gatgatcaga tgtgtacatc ggatacaagt   9180
atatatgcaa tcgcgactg cgcaatggct agaaatcctt tttggggaac gatggtacgt   9240
ttagagacaa ttcataatgc ggttacacac gctcaaattg tcgcaagtag catctgtggc   9300
acatcaacac cagcaccaac cccaccacgg ttctggtctg atcttaaagg gatggcgctg   9360
caaggacttg gtgctctaaa ggactacgat aaactcgttg ttgcaattaa taacgaaact   9420
cttgaactag aagtccttgc gtacaagcag gagcgactga ttgcaactga gacaataaat   9480
ttgcctaaac gtcaaggtgc gcttgcaggg agtataaaat tacctgatta gcaatgatgc   9540
tcagccactc gaaccaacgg tcgcgatagg gacggcagtt acctgccgcc ccccgcactc   9600
cgtacgtgcg gaactaccgc gtaaaatgtg gcccaggctg ttatgtggcg cttgggcggg   9660
gaagtattgc catatttggt gatgaccgtt ttctacgcca cataaatcgg tggtggctat   9720
ggtgggattt cccttgctga aatgggagat ccgatcatgt tcgagctctt attcaaatac   9780
actgctgtgt tggcggtaag cgttctcgag ctcatagtcc acgacgcccg tgattttgta   9840
gccctggccg acgccagca ggtaggccga caggctcatg ccggccgccg ccgccttttc   9900
ctcaatcgct cttcgttcgt ctggaaggca gtacaccttg ataggtgggc tgcccttcct   9960
ggttggcttg gtttcatcag ccatccgctt gccctcatct gttacgccgg cggtagccgg  10020
ccagcctcgc agagcaggat tcccgttgag caccgccagg tgcgaataag ggacagtgaa  10080
gaaggaacac ccgctcgcgg gtgggcctac ttcacctatc ctgcccggct gacgccgttg  10140
gatacaccaa ggaaagtcta cacgaaccct ttggcaaaat cctgtatatc gtgcgaaaaa  10200
ggatggatat accgaaaaaa tcgctataat gaccccgaag cagggttatg cagcggaaaa  10260
```

-continued

```
gcgctgcttc cctgctgttt tgtggaatat ctaccgactg gaaacaggca aatgcaggaa    10320
attactgaac tgaggggaca ggcgagagag gatcaatggc tatctggggg accgagggct    10380
gtcgctgcgc caaggcacga ttggagatcc cctatgcggt gtgaaatacc gcacagatgc    10440
gtaaggagaa aataccgcat caggcgctct tccgcttcct cgctcactga ctcgctgcgc    10500
tcggtcgttc ggctgcggcg agcggtatca gctcactcaa aggcggtaat acggttatcc    10560
acagaatcag gggataacgc aggaaagaac atgtgagcaa aaggccagca aaaggccagg    10620
aaccgtaaaa aggccgcgtt gctggcgttt ttccataggc tccgcccccc tgacgagcat    10680
cacaaaaatc gacgctcaag tcagaggtgg cgaaacccga caggactata aagataccag    10740
gcgtttcccc ctggaagctc cctcgtgcgc tctcctgttc cgaccctgcc gcttaccgga    10800
tacctgtccg cctttctccc ttcgggaagc gtggcgcttt ctcatagctc acgctgtagg    10860
tatctcagtt cggtgtaggt cgttcgctcc aagctgggct gtgtgcacga accccccgtt    10920
cagcccgacc gctgcgcctt atccggtaac tatcgtcttg agtccaaccc ggtaagacac    10980
gacttatcgc cactggcagc agccactggt aacaggatta gcagagcgag gtatgtaggc    11040
ggtgctacag agttcttgaa gtggtggcct aactacggct acactagaag gacagtattt    11100
ggtatctgcg ctctgctgaa gccagttacc ttcggaaaaa gagttggtag ctcttgatcc    11160
ggcaaacaaa ccaccgctgg tagcggtggt ttttttgttt gcaagcagca gattacgcgc    11220
agaaaaaaag gatctcaaga agatcctttg atcttttcta cggggtctga cgctcagtgg    11280
aacgaaaact cacgttaagg gattttggtc atgagattat caaaaaggat cttcacctag    11340
atccttttaa attaaaaatg aagttttaaa tcaatctaaa gtatatatga gtaaacttgg    11400
tctgacagtt accaatcgat tggtcggtca tttcgaaccc cagagtcccg ctcagaagaa    11460
ctcgtcaaga aggcgataga aggcgatgcg ctgcgaatcg ggagcggcga taccgtaaag    11520
cacgaggaag cggtcagccc attcgccgcc aagctcttca gcaatatcac gggtagccaa    11580
cgctatgtcc tgatagcggt ccgccacacc cagccggcca cagtcgatga atccagaaaa    11640
gcggccattt tccaccatga tattcggcaa gcaggcatcg ccatgggtca cgacgagatc    11700
ctcgccgtcg ggcatgcgcg ccttgagcct ggcgaacagt tcggctggcg cgagcccctg    11760
atgctcttcg tccagatcat cctgatcgac aagaccggct tccatccgag tacgtgctcg    11820
ctcgatgcga tgtttcgctt ggtggtcgaa tgggcaggta gccggatcaa gcgtatgcag    11880
ccgccgcatt gcatcagcca tgatggatac tttctcggca ggagcaaggt gagatgacag    11940
gagatcctgc cccggcactt cgcccaatag cagccagtcc cttcccgctt cagtgacaac    12000
gtcgagcaca gctgcgcaag gaacgcccgt cgtggccagc cacgatagcc gcgctgcctc    12060
gtcctgcagt tcattcaggg caccggacag gtcggtcttg acaaaaagaa ccgggcgccc    12120
ctgcgctgac agccggaaca cggcggcatc agagcagccg attgtctgtt gtgcccagtc    12180
atagccgaat agcctctcca cccaagcggc cggagaacct gcgtgcaatc catcttgttc    12240
aatcatgcga aacgatcctc atcctgtctc ttgatcagat cttgatcccc tgcgccatca    12300
gatccttggc ggcaagaaag ccatccagtt tactttgcag gcttccc                  12348
```

BIOCATALYTIC OXIDATION PROCESS WITH ALKL GENE PRODUCT

FIELD OF THE INVENTION

The invention relates to a biocatalytic method for oxidizing organic compounds using an alkL gene product, and also microorganisms used in this method.

PRIOR ART

The OCT plasmid of *Pseudomonas putida*, for example, contains an alkL gene. This plasmid encodes, moreover, gene products which are responsible for alkane degradation. These alkane degradation genes are arranged on the *Pseudomonas* OCT plasmid in two alk operons; the first encodes the gene products AlkB, AlkF, AlkG, AlkH, AlkJ, AlkK and AlkL, the second encoding AlkS and AlkT, wherein AlkS has a regulatory function on the expression of the first alk operon. For a more detailed overview and the function of further genes of this alk operon, see Chen et al., J. Bacteriol. 1995 December, 177(23):6894-901.

In addition, EP277674 discloses a microbiological method for the terminal hydroxylation of apolar aliphatic compounds having 6 to 12 carbon atoms, such as the production of 1-octanol, by means of micro-organisms of the genus *Pseudomonas putida*, which are resistant to apolar phases, wherein, inter alia, a plasmid pGEc47 having the alkL gene is used, which carries the two alk operons from *Pseudomonas putida* as well. The control of the alkL gene is under the control of the native operon promoter and is therefore transcribed and translated together with alkB, alkF, alkG, alkH, alkJ and alkK.

WO2002022845 describes a method for producing N-benzyl-4-hydroxypiperidine by hydroxylating N-benzyl-4-piperidine by *E. coli* cells that carry the above-mentioned plasmid pGEc47.

EP0502524 describes a microbiological method for the terminal hydroxylation of ethyl groups on aromatic 5- or 6-membered ring heterocycles using the production of various gene products of the alk operons, for instance, via the plasmid pGEc41, for example, which encodes the gene products of alkB, alkG, alkH, alkT and alkS, but not alkL. The same application additionally describes a plasmid pGMK921 that, like pGEc41, contains the genes for alkB, alkG, alkH, alkT and alkS—but not alkL, the expression of which, however, is possible not only by alkane induction by the native promoter, but also by IPTG induction by the tac promoter (cf. U.S. Pat. No. 5,306,625 too).

Schneider et al., in Appl Environ Microbiol. 1998 October; 64(10):3784-90, describe a bioconversion of saturated fatty acids to the ω-1-, ω-2- and ω-3-hydroxy fatty acids thereof in *E. coli* using a cytochrome-P-450BM-3 monooxygenase and the abovementioned plasmid pGEc47.

Favre-Bulle et al., in Nature Bio/Technology 9, 367-371 (April 1991), describe a method for producing 1-octanoic acid by biotransformation of octane with an *E. coli* bacterium carrying pGEc47 used as biocatalyst. Both alk operons are expressed completely in the method described.

The same approach is followed by Rothen et al., in Biotechnol Bioeng. 1998 May 20; 58(4):356-65.

It is a disadvantage of the described prior art that gene products that make no significant contribution to the desired oxidation process are produced superfluously by the cell used as biocatalyst and therefore decrease the performance thereof.

Furthermore, the unnecessarily co-synthesized alk gene products may contain unwanted enzyme activities that are detrimental to the desired product formation, for instance in that intermediate product escapes as unwanted byproducts. In the desired ω-hydroxylation of an organic radical, the alkJ gene product leads to formation of the corresponding aldehyde. In the case of, for example, the simultaneous presence of the alkH gene product, the resultant aldehyde is further oxidized to the carboxylic acid. Thus, in EP0502524, for generating the desired hydroxylated method product, only the gene products of alkB, alkG and alkT are required, whereby, e.g., the genes alkF, alkJ, alkH and alkS are superfluous. It is disadvantageous here, furthermore, that the synthesis of further alk gene products makes high demands of the metabolic capacity of the host. AlkJ, e.g., is an FAD-containing enzyme (Chen et al., J. Bacteriol, (1995), 6894-6901). However, the FAD pool of the host is already burdened by the unavoidable production of alkT, which likewise contains FAD. Since the FAD synthesis capacity is limited in *E. coli*, e.g., and is likewise required for existential cell metabolism, the cell is avoidably burdened in the case of unnecessary alkJ production.

Furthermore, the gene products of alkB, alkJ and alkH are cytoplasmic-membrane-located or cytoplasmic-membrane-associated. The respiration chain is also located in this region. An excess production of membrane proteins leads from changes in the cell membrane to detachment of membrane vesicles which migrate into the cytosol (Nieboer et al., Molecular Microbiology (1993) 8(6), 1039-1051).

This finally leads to premature lysis of the cells (Wubbolts et al., Biotechnology and Bioengineering (1996), Vol. 52, 301-308), all the more so in the high cell density fermentation indispensible for industrial processes.

Similarly, in Schneider et al., the gene products of alkB, alkF, alkG, alkH, alkJ, alkK, alkS and alkT are superfluously co-synthesized, since the enzyme actually used for the desired reaction is the cytochrome-P-450BM-3 monooxygenase.

With regard to industrial processes, the use of plasmid-encoded metabolic pathways is difficult. With increasing size of fermenter volume, the use of antibiotics for maintaining a selection pressure, which improves the plasmid stability, firstly becomes very expensive, and secondly, effluent-critical. Large fermentations therefore virtually proceed always without any addition of antibiotics.

In order, nevertheless, to ensure the genetic stability of the artificial oxidative metabolic pathway, integration of the genes used into the genome of the host organism is desirable. Such an approach succeeds better the smaller is the gene construct that is to be integrated. Since the minimal gene set alkBGTL considered here already has a considerable size, any further nucleotide sequence that is not absolutely necessary must be avoided.

In addition to reducing the scope of the necessary molecular biology work and increasing the probability of success thereof, a construct as small as possible also contributes to the genomic stability of the host organism.

It was an object of the invention to provide a method which is able to overcome at least one of said disadvantages of the prior art.

DESCRIPTION OF THE INVENTION

Surprisingly it has been found that the method described hereinafter and the genetically modified cells make a contribution to achieving the object in question.

The present invention therefore relates to a method for producing an oxidized organic substance, using an alkL gene product as described in Claim 1 and also the recombinant cells used in this method.

The invention further relates to the use of an alkL gene product for increasing the oxidation rate.

Advantages are the optimal utilization of the resources present in the method, for example with respect to cellular metabolism, in particular under high cell density fermentation conditions.

The present invention describes a method for oxidizing an organic substance using at least one oxidizing enzyme and at least one alkL gene product, characterized in that the alkL gene product is provided independently of at least one other gene product encoded by the alk operon containing the alkL gene.

The alk genes described in association with this invention encode protein sequences which are termed analogously AlkX. If a plurality of genes alkX, alkY and alkZ are described simultaneously, the nomenclature alkXYZ or, analogously with the proteins, AlkXYZ is used.

The expression "oxidation of an organic substance" in association with the present invention is taken to mean, for example, a hydroxylation or epoxidation, the reaction of an alcohol to form an aldehyde or ketone, the reaction of an aldehyde to form a carboxylic acid or the hydration of a double bond. Likewise, multistage oxidation processes are also summarized thereunder, as can be achieved, in particular, by using a plurality of oxidizing enzymes, such as, for example, the hydroxylation of an alkyl radical at a plurality of sites, e.g. at the ω position and ω-1 position, catalysed by various monooxygenases.

The expression "using at least one oxidizing enzyme and at least one alkL gene product" is taken to mean, in association with the present invention, the targeted provision of the enzymes and gene products, more precisely in a form how each individual enzyme or gene product considered separately does not occur in free nature. This can proceed, for example, by heterologous production or overproduction of the proteins used in a cell or by providing at least partly purified proteins; however, an altered environment compared to the enzyme occurring in free nature is also included here, for instance in the form that the natural cell containing the enzyme was modified, in such a manner that it produces, for example, certain other proteins in modified form, such as, for example, weakened or strengthened, or provided with point mutations.

The expression "alkL gene product", in association with the present invention, is taken to mean proteins that meet at least one of the two conditions hereinafter:

1.) The protein is identified as a member of the super-family of the OmpW proteins (protein family 3922 in the Conserved Domain Database (CDD) of the National Center for Biotechnology Information (NCBI)), wherein this assignment is made by an alignment of the amino acid sequence of the protein with the database entries present in the CDD of the NCBI that had been deposited by 22.03.2010, using the standard search parameter, an e value less than 0.01 and using the algorithm "blastp 2.2.23+", 2.) in a search for the conserved protein domains contained in the amino acid sequence of interest in the NCBI CDD (Version 2.20) by means of RPS-BLAST, the presence of the conserved domain "OmpW, Outer membrane protein W" (COG3047) with an e value less than $1\times10^{-5}$ is observed (a domain hit).

The expression "provided independently of at least one other gene product encoded by the alk operon containing the alkL gene", in association with the present invention, is taken to mean provision of the alkL gene product which is independent of at least one further alk gene product that in a naturally occurring form is coupled to the formation of the alkL gene product. For example, in one operon comprising the genes alkBFGHJKL, the alk gene products of respectively alkBFGHJ and K are coupled to the formation of the alkL gene product, since they are provided via the same promoter.

All percentages (%) given are percent by mass, unless stated otherwise.

The method according to the invention, depending on the oxidizing enzyme used, may be used for the oxidation of any organic substances which are accepted as a substrate by this oxidizing enzyme; preferred organic substances are selected from the group containing, preferably consisting of, branched or unbranched, preferably unbranched, saturated or unsaturated, preferably saturated, optionally substituted alkanes, alkenes, alkynes, alcohols, aldehydes, ketones, carboxylic acids, esters of carboxylic acids, amines and epoxides, wherein these have preferably 3 to 22, in particular 6 to 18, more preferably 8 to 14, in particular 12, carbon atoms.

Particularly preferred organic substances in the method according to the invention are selected from the group containing, preferably consisting of, carboxylic acids and corresponding esters thereof, in particular having 3 to 22, preferably 6 to 18, particularly preferably 8 to 14, carbon atoms, in particular carboxylic acids of alkanes, in particular unbranched carboxylic acids of alkanes, in particular lauric acid and esters thereof, in particular lauric acid, methyl ester and lauric acid, ethyl ester, decanoic acid, esters of decanoic acid, myristic acid and esters of myristic acid, unsubstituted alkanes having 3 to 22, preferably 6 to 18, particularly preferably 8 to 14, carbon atoms, preferably unbranched, in particular selected from the group containing, preferably consisting of, octane, decane, dodecane and tetradecane, unsubstituted alkenes having 3 to 22, preferably 6 to 18, particularly preferably 8 to 14, carbon atoms, preferably unbranched, in particular selected from the group containing, preferably consisting of, trans-oct-1-ene, trans-non-1-ene, trans-dec-1-ene, trans-undec-1-ene, trans-dodec-1-ene, trans-tridec-1-ene, trans-tetradec-1-ene, cis-oct-1-ene, cis-non-1-ene, cis-dec-1-ene, cis-undec-1-ene, cis-dodec-1-ene, cis-tridec-1-ene, cis-tetradec-1-ene, trans-oct-2-ene, trans-non-2-ene, trans-dec-2-ene, trans-undec-2-ene, trans-dodec-2-ene, trans-tridec-2-ene and trans-tetradec-2-ene, trans-oct-3-ene, trans-non-3-ene, trans-dec-3-ene, trans-undec-3-ene, trans-dodec-3-ene, trans-tridec-3-ene and trans-tetradec-3-ene, trans-oct-4-ene, trans-non-4-ene, trans-dec-4-ene, trans-undec-4-ene, trans-dodec-4-ene, trans-tridec-4-ene, trans-tetradec-4-ene, trans-dec-5-ene, trans-undec-5-ene, trans-dodec-5-ene, trans-tridec-5-ene, trans-tetradec-5-ene, trans-dodec-6-ene, trans-tridec-6-ene, trans-tetradec-6-ene, and trans-tetradec-7-ene, particularly preferably consisting of trans-oct-1-ene, trans-dec-1-ene, trans-dodec-1-ene, trans-tetradec-1-ene, cis-oct-1-ene, cis-dec-1-ene, cis-dodec-1-ene, cis-tetradec-1-ene, trans-oct-2-ene, trans-dec-2-ene, trans-dodec-2-ene and trans-tetradec-2-ene, trans-oct-3-ene, trans-dec-3-ene, trans-dodec-3-ene, and trans-tetradec-3-ene, trans-oct-4-ene, trans-dec-4-ene, trans-dodec-4-ene, trans-tetradec-4-ene, trans-dec-5-ene, trans-dodec-5-ene, trans-tetradec-5-ene, trans-dodec-6-ene, trans-tetradec-6-ene and trans-tetradec-7-ene, unsubstituted monohydric alcohols having 3 to 22, preferably 6 to 18, particularly preferably 8 to 14, carbon atoms, preferably unbranched, in particular selected from the group containing, preferably consisting of, 1-octanol, 1-nonanol, 1-decanol, 1-undecanol, 1-dodecanol, 1-tridecanol and 1-tetradecanol, particularly preferably consisting of 1-octanol, 1-decanol, 1-dodecanol and 1-tetradecanol, unsubstituted aldehydes having 3 to 22, preferably 6 to 18, particularly preferably 8 to 14, carbon atoms, preferably unbranched, in particular selected from the group containing, preferably consisting of, octanal, nonanal, decanal, dodecanal and tetradecanal, unsubstituted monobasic amines having 3 to 22, preferably 6 to 18, particularly preferably 8 to 14, carbon atoms, preferably unbranched, in particular selected from the group containing, preferably consisting of, 1-aminooctane, 1-aminononane, 1-amino-decane, 1-aminoundecane, 1-aminododecane, 1-amino-tridecane and 1-aminotetradecane, particularly preferably consisting of 1-aminooctane, 1-aminodecane, 1-aminododecane and 1-aminotetradecane, and also substituted compounds that, in particular, as further substituents, carry one or more hydroxyl, amino, keto, carboxyl, cyclopropyl radicals or epoxy functions, in particular selected from the group containing, preferably consisting of, 1,8-octanediol, 1,9-nonanediol, 1,10-decanediol, 1,11-undecanediol, 1,12-dodecanediol, 1,13-tridecanediol, 1,14-tetradecanediol, 8-amino-[1-octanol], 9-amino-[1-nonanol], 10-amino-[1-dodecanol], 11-amino-[1-undecanol], 12-amino-[1-dodecanol], 13-amino-[1-tridecanol], 14-amino-[1-tetradecanol], 8-hydroxy-[1-octanal], 9-hydroxy-[1-nonanal], 10-hydroxy-[1-decanal], 11-hydroxy-[1-undecanal], 12-hydroxy-[1-dodecanal], β-hydroxy-[1-tridecanal], 14-hydroxy-[1-tetradecanal], 8-amino-[1-octanal], 9-amino-[1-nonanal], 10-amino-[1-decanal], 11-amino-[1-undecanal], 12-amino-[1-dodecanal], 13-amino-[1-tridecanal], 14-amino-[1-tetradecanal], 8-hydroxy-1-octanoic acid, 9-hydroxy-1-nonanoic acid, 10-hydroxy-1-decanoic acid, 11-hydroxy-1-undecanoic acid, 12-hydroxy-1-dodecanoic acid, β-hydroxy-1-undecanoic acid, 14-hydroxy-1-tetradecanoic acid, 8-hydroxy-1-octanoic acid, methyl ester, 9-hydroxy-1-nonanoic acid, methyl ester, 10-hydroxy-1-decanoic acid, methyl ester, 11-hydroxy-1-undecanoic acid, methyl ester, 12-hydroxy-1-dodecanoic acid, methyl ester, 13-hydroxy-1-undecanoic acid, methyl ester, 14-hydroxy-1-tetradecanoic acid, methyl ester, 8-hydroxy-1-octanoic acid, ethyl ester, 9-hydroxy-1-nonanoic acid, ethyl ester, 10-hydroxy-1-decanoic acid, ethyl ester, 11-hydroxy-1-undecanoic acid, ethyl ester, 12-hydroxy-1-dodecanoic acid, ethyl ester, 13-hydroxy-1-undecanoic acid, ethyl ester and 14-hydroxy-1-tetra-decanoic acid, ethyl ester, particularly preferably consisting of 1,8-octanediol, 1,10-decanediol, 1,12-dodecanediol, 1,14-tetradecane-diol, 8-amino-[1-octanol], 10-amino-[1-dodecanol], 12-amino-[1-dodecanol], 14-amino-[1-tetradecanol], 8-hydroxy-[1-octanal], 10-hydroxy-[1-decanal], 12-hydroxy-[1-dodecana, 14-hydroxy-[1-tetradecanal], 8-amino-[1-octanal], 10-amino-[1-decanal], 12-amino-[1-dodecanal], 14-amino-[1-tetradecanal], 8-hydroxy-1-octanoic acid, 10-hydroxy-1-decanoic acid, 12-hydroxy-1-dodecanoic acid, 14-hydroxy-1-tetra-decanoic acid, 8-hydroxy-1-octanoic acid, methyl ester, 10-hydroxy-1-decanoic acid, methyl ester, 12-hydroxy-1-dodecanoic acid, methyl ester, 14-hydroxy-1-tetra-decanoic acid, methyl ester, 8-hydroxy-1-octanoic acid, ethyl ester, 10-hydroxy-1-decanoic acid, ethyl ester, 12-hydroxy-1-dodecanoic acid, ethyl ester and 14-hydroxy-1-tetradecanoic acid, ethyl ester, wherein lauric acid and esters thereof, in particular lauric acid, methyl ester and lauric acid, ethyl ester, are particularly preferred.

By means of the method according to the invention, depending on the oxidizing enzyme used and the organic substance used, various oxidation products may be produced, in particular alcohols, aldehydes, ketones and carboxylic acids. These oxidation products may be obtained, for example, by means of the method according to the invention by reacting an organic substance listed hereinafter to form the following:

alkane/alkene/alkyne to form alcohol (for example in the presence of a monooxygenase)

alcohol to form aldehyde (for example in the presence of an alcohol dehydrogenase or alcohol oxidase)

alcohol to form ketone (for example in the presence of an alcohol dehydrogenase or alcohol oxidase)

aldehyde to form carboxylic acid (for example in the presence of an aldehyde dehydrogenase)

epoxide to form cyanohydrin (for example in the presence of a halohydrin dehalogenase)

Within this context, preference is given to producing alcohols and aldehydes, preferably alcohols, in particular ω-alcohols, very particularly ω-hydroxy-carboxylic acids using the method according to the invention, in particular in the form of a hydroxylation reaction.

In the method according to the invention, organic substances, in particular carboxylic acids and esters of carboxylic acids, may be oxidized advantageously at the ω-position.

In the method according to the invention, all oxidizing enzymes known to those skilled in the art may be used, since the function of the alkL gene product provided is independent thereof. Such enzymes are well known to those skilled in the art under the name oxidoreductase and may be found in enzyme class EC 1.X.X.X of the systematic nomenclature of the Enzyme Commission of the International Union of Biochemistry and Molecular Biology.

Preferably, in the method according to the invention, the oxidizing enzyme used is an alkane monooxygenase, a xylene monooxygenase, an aldehyde dehydrogenase, an alcohol oxidase or an alcohol dehydrogenase, preferably an alkane monooxygenase.

A suitable gene for a xylene monooxygenase is, for example, the xylM or the xylA gene, wherein a plasmid containing these two genes has the GENBANK Accession No. M37480.

A particularly preferred alkane monooxygenase within this context is characterized in that it is a cytochrome-P450 monooxygenase, in particular a cytochrome-P450 monooxygenase from yeasts, in particular *Pichia*, *Yarrowia* and *Candida*, for example from *Candida tropicalis* or *Candida maltose*, or from plants, for example from *Cicer arietinum* L., or from mammals, for example from *Rattus norvegicus*, in particular CYP4A1. The gene sequences of suitable cytochrome-P450 monooxygenases from *Candida tropicalis* are disclosed, for example, in WO-A-00/20566, while the gene sequences of suitable cytochrome-P450 monooxygenases from chickpea may be found, for example, in Barz et al. in "Cloning and characterization of eight cytochrome P450 cDNAs from chickpea (*Cicer arietinum* L.) cell suspension cultures", Plant Science, Vol. 155, pages 101-108 (2000).

A further preferred alkane monooxygenase is encoded by the alkB gene of the alk operon from *Pseudomonas putida* GPo1.

The isolation of the alkB gene sequence is described, for example, by van Beilen et al. in "Functional Analysis of Alkane Hydroxylases from Gram-Negative and Gram-Positive Bacteria", Journal of Bacteriology, Vol. 184 (6), pages 1733-1742 (2002). Further homologues of the alkB gene can also be found from van Beilen et al. in "Oil & Gas Science and Technology", Vol. 58 (4), pages 427-440 (2003).

In addition, preferred alkane monooxygenases are those alkB gene products which are encoded by alkB genes from organisms selected from the group of the Gram-negative bacteria, in particular from the group of the Pseudomonads, there from the genus *Pseudomonas*, particularly *Pseudomonas mendocina*, the genus *Oceanicaulis*, preferably *Oceanicaulis alexandrii* HTCC2633, the genus *Caulobacter*, preferably *Caulobacter* sp. K31, the genus *Marinobacter*, preferably *Marinobacter aquaeolei*, particularly preferably *Marinobacter aquaeolei* VT8, the genus *Alcanivorax*, preferably *Alcanivorax borkumensis*, the genus *Acetobacter, Achromobacter, Acidiphilium, Acidovorax, Aeromicrobium, Alkalilimnicola, Alteromonadales, Anabaena, Aromatoleum, Azoarcus, Azospirillum, Azotobacter, Bordetella, Bradyrhizobium, Burkholderia, Chlorobium, Citreicella, Clostridium, Colwellia, Comamonas, Conexibacter, Congregibacter, Corynebacterium, Cupriavidus, Cyanothece, Delftia, Desulfomicrobium, Desulfonatronospira, Dethiobacter, Dinoroseobacter, Erythrobacter, Francisella, Glaciecola, Gordonia, Grimontia, Hahella, Haloterrigena, Halothiobacillus, Hoeflea, Hyphomonas, Janibacter, Jannaschia, Jonquetella, Klebsiella, Legionella, Limnobacter, Lutiella, Magnetospirillum, Mesorhizobium, Methylibium, Methylobacterium, Methylophaga, Mycobacterium, Neisseria, Nitrosomonas, Nocardia, Nostoc, Novosphingobium, Octadecabacter, Paracoccus, Parvibaculum, Parvularcula, Peptostreptococcus, Phaeobacter, Phenylobacterium, Photobacterium, Polarornonas, Prevotella, Pseudoalteromonas, Pseudovibrio, Psychrobacter, Psychroflexus, Ralstonia, Rhodobacter, Rhodococcus, Rhodoferax, Rhodomicrobium, Rhodopseudornonas, Rhodospirillum, Roseobacter, Roseovarius, Ruegeria, Sagittula, Shewanella, Silicibacter, Stenotrophomonas, Stigmatella, Streptomyces, Sulfitobacter, Sulfurimonas, Sulfurovum, Synechococcus, Thalassiobium, Thermococcus, Thermomonospora, Thioalkalivibrio, Thiobacillus, Thiomicrospira, Thiomonas, Tsukarnurella, Vibrio* or *Xanthomonas*, wherein those from *Alcanivorax borkumensis, Oceanicaulis alexandrii* HTCC2633, *Caulobacter* sp. K31 and *Marinobacter aquaeolei* VT8 are particularly preferred. In this context, it is advantageous if, in addition to AlkB, alkG and alkT gene products are provided; these can either be the gene products isolatable from the organism contributing the alkB gene product, or else the alkG and alkT from *Pseudomonas putida* GPo1.

A preferred alcohol dehydrogenase is, for example, the enzyme (EC 1.1.99.8) encoded by the alkJ gene, in particular the enzyme encoded by the alkJ gene from *Pseudomonas putida* GPo1 (van Beilen et al., Molecular Microbiology, (1992) 6(21), 3121-3136). The gene sequences of the alkJ genes from *Pseudomonas putida* GPo1, *Alcanivorax borkumensis, Bordetella parapertussis, Bordetella bronchiseptica* or from *Roseobacter denitrificans* can be found, for example, in the KEGG gene database (Kyoto Encyclopedia of Genes and Genomes). In addition, preferred alcohol dehydrogenases are those which are encoded by alkJ genes from organisms selected from the group of the Gram-negative bacteria, in particular from the group of the Pseudomonads, there from the genus *Pseudomonas*, particularly *Pseudomonas mendocina*, the genus *Oceanicaulis*, preferably *Oceanicaulis alexandrii* HTCC2633, the genus *Caulobacter*, preferably *Caulobacter* sp. K31, the genus *Marinobacter*, preferably *Marinobacter aquaeolei*, particularly preferably *Marinobacter aquaeolei* VT8, the genus *Alcanivorax*, preferably *Alcanivorax borkumensis*, the genus *Acetobacter, Achromobacter, Acidiphilium, Acidovorax, Aeromicrobium, Alkalilimnicola, Alteromonadales, Anabaena, Aromatoleum, Azoarcus, Azospirillum, Azotobacter, Bordetella, Bradyrhizobium, Burkholderia, Chlorobium, Citreicella, Clostridium, Colwellia, Comamonas, Conexibacter, Congregibacter, Corynebacterium, Cupriavidus, Cyanothece, Delftia, Desulfomicrobium, Desulfonatronospira, Dethiobacter, Dinoroseobacter, Erythrobacter, Francisella, Glaciecola, Gordonia, Grimontia, Hahella, Haloterrigena, Halothiobacillus, Hoeflea, Hyphomonas, Janibacter, Jannaschia, Jonquetella, Klebsiella, Legionella, Limnobacter, Lutiella, Magnetospirillum, Mesorhizobium, Methylibium, Methylobacterium, Methylophaga, Mycobacterium, Neisseria, Nitrosomonas, Nocardia, Nostoc, Novosphingobium, Octadecabacter, Paracoccus, Parvibaculum, Parvularcula, Peptostreptococcus, Phaeobacter, Phenydobacterium, Photobacterium, Polaromonas, Prevotella, Pseudoalteromonas, Pseudovibrio, Psychrobacter, Psychroflexus, Ralstonia, Rhodobacter, Rhodococcus, Rhodoferax, Rhodomicrobium, Rhodopseudomonas, Rhodospirillum, Roseobacter, Roseovarius, Ruegeria, Sagittula, Shewanella, Silicibacter, Stenotrophomonas, Stigmatella, Streptomyces, Sulfitobacter, Sulfurimonas, Sulfurovum, Synechococcus, Thalassiobium, Thermococcus, Thermomonospora, Thioalkalivibrio, Thiobacillus, Thiomicrospira, Thiomonas, Tsukarnurella, Vibrio* or *Xanthomonas*.

Preferred alkL gene products used in the method according to the invention are characterized in that the production of the alkL gene product is induced in the native host by dicyclopropyl ketone; in this context it is, in addition, preferred that the alkL gene is expressed as part of a group of genes, for example in a regulon, such as, for instance, an operon. The alkL gene products used in the method according to the invention are preferably encoded by alkL genes from organisms selected from the group of the Gram-negative bacteria, in particular the group containing, preferably consisting of, Pseudomonads, particularly *Pseudomonas putida*, in particular *Pseudomonas putida* GPo1 and P1, *Azotobacter, Desulfitobacterium, Burkholderia*, preferably *Burkholderia cepacia, Xanthomonas, Rhodobacter, Ralstonia, Delftia* and *Rickettsia*, the genus *Oceanicaulis*, preferably *Oceanicaulis alexandrii* HTCC2633, the genus *Caulobacter*, preferably *Caulobacter* sp. K31, the genus *Marinobacter*, preferably *Marinobacter aquaeolei*, particularly preferably *Marinobacter aquaeolei* VT8 and the genus *Rhodopseudomonas*.

It is advantageous if the alkL gene product originates from a different organism from the oxidizing enzyme used according to the invention.

In this context, very particularly preferred alkL gene products are encoded by the alkL genes from *Pseudomonas putida* GPo1 and P1, which are given by Seq ID No. 1 and Seq ID No. 3, and also proteins having the polypeptide sequence Seq ID No. 2 or Seq ID No. 4 or having a polypeptide sequence in which up to 60%, preferably up to 25%, particularly preferably up to 15%, in particular up to 10, 9, 8, 7, 6, 5, 4, 3, 2, 1% of the amino acid residues are modified in comparison with Seq ID No. 2 or Seq ID No. 4 by deletion, insertion, substitution or a combination thereof and which products still have at least 50%, preferably 65%, particularly preferably 80%, in particular more than 90%, of the activity of the protein having the respective reference sequence Seq ID No. 2 or Seq ID No. 4, wherein 100% activity of the reference protein is taken to mean the increase of the activity of the cells used as biocatalyst, that is to say the amount of substance reacted per unit time, based on the cell weight used (units per gram of cell dry weight [U/gCDW]), compared with the activity of the biocatalyst without the presence of the reference protein, more precisely in a system as described in the exemplary embodiments, in which the oxidizing enzymes used for converting lauric acid, methyl ester to 12-hydroxylauric acid, methyl ester in an E. coli cell are the gene products of alkBGT from P. putida GPo1. A method of choice for determining the oxidation rate may be found in the exemplary embodiments.

The definition of the unit here is the definition customary in enzyme kinetics. One unit of biocatalyst reacts 1 µmol of substrate in 1 minute to form the product.

1 U=1 µmol/min

Modifications of amino acid residues of a given poly-peptide sequence that do not lead to any substantial changes of the properties and function of the given polypeptide are known to those skilled in the art. For instance, some amino acids, for example, can frequently be exchanged for one another without problem; examples of such suitable amino acid substitutions are:

Ala for Ser; Arg for Lys; Asn for Gln or His; Asp for Glu; Cys for Ser; Gln for Asn; Glu for Asp; Gly for Pro; His for Asn or Gln; Ile for Leu or Val; Leu for Met or Val; Lys for Arg or Gln or Glu; Met for Leu or Ile; Phe for Met or Leu or Tyr; Ser for Thr; Thr for Ser; Trp for Tyr; Tyr for Trp or Phe; Val for Ile or Leu. It is likewise known that modifications particularly at the N- or C-terminus of a polypeptide in the form of, for example, amino acid insertions or deletions frequently have no substantial effect on the function of the polypeptide.

A preferred method according to the invention is characterized in that the further gene product is selected from at least one of the group consisting of AlkB, AlkF, AlkG, AlkH, AlkJ, and AlkK,
in particular consisting of AlkF, AlkG, AlkH, AlkJ and AlkK, wherein further gene products are selected in particular from the group containing, preferably consisting of, the gene combinations: alkBF, alkBG, alkFG, alkBJ, alkFJ, alkGJ, alkBH, alkFH, alkGH, alkJH, alkBK, alkFK, alkGK, alkJK, alkHK, alkBFG, alkBFJ, alkBFH, alkBFK, alkBGJ, alkFGJ, alkBGH, alkFGH, alkBGK, alkFGK, alkBJH, alkFJH, alkGJH, alkBJK, alkFJK, alkGJK, alkFHK, alkBHK, alkFHK, alkGHK, alkBGJH, alkBGJK, alkBGHK, alkBFGJ, alkBFGH, alkFGJH, alkBFGK, alkFGJK, alkGJHK, alkBFJH, alkBFJK, alkFJHK, alkBFHK, alkBFGJH, alkBFGJK and alkBFGJHK,
in particular alkFHJK and alkBFGHJK.

It is advantageous for the method according to the invention if the oxidizing enzyme and the alkL gene product are provided by a microorganism. In this case, the two enzymes can each be provided separately, each in one microorganism, or together in one microorganism, wherein the latter is preferred. Therefore, a preferred method according to the invention is characterized in that it is carried out in at least one microorganism or in a medium surrounding the at least one microorganism, which microorganism provides the oxidizing enzyme and the alkL gene product. In this context it is preferred that the oxidizing enzyme and the alkL gene product are provided recombinantly in the at least one micro-organism.

The remarks now following on recombinant production relate not only to the oxidizing enzyme but also to the alkL gene product.

In principle, a recombinant production may be achieved by increasing the number of copies of the gene sequence or the gene sequences which encode the protein, using a modified promoter, modifying the codon usage of the gene, increasing in various ways the half-life of the mRNA or of the enzyme, modifying the regulation of expression of the gene or using a gene or allele which encodes a corresponding protein, and optionally combining these measures. Cells having such a gene provision are generated, for example, by transformation, transduction, conjugation or a combination of these methods using a vector which contains the desired gene, an allele of this gene or parts thereof, and a promoter which makes possible the expression of the gene. Heterologous expression is made possible, in particular, by integrating the gene or the alleles into the chromosome of the cell or a vector replicating extrachromosomally. A survey of the possibilities of recombinant production in cells for the example of isocitrate lyase is given in EP0839211 which is hereby incorporated by reference and the disclosure thereof with respect to the possibilities of recombinant production in cells forms a part of the disclosure of the present invention.

The provision and/or production and/or expression of the abovementioned, and all hereinafter mentioned, proteins and/or genes is detectable using 1- and 2-dimensional gel electrophoresis and subsequent optical identification of the protein concentration using corresponding evaluation software in the gel. If the expression performance found is based solely on increasing the expression of the corresponding gene, the recombinant expression can be quantified in a simple manner by comparison of the 1- or 2-dimensional protein separations between wild type and genetically modified cell. A customary method for preparing the protein gels in the case of coryneform bacteria and for identifying the proteins is the procedure described by Hermann et al. (Electrophoresis, 22: 1712.23 (2001)). The protein concentration can likewise be analysed by Western-Blot hybridization with an antibody specific for the protein to be detected (Sambrook et al., Molecular Cloning: a laboratory manual, 2nd Ed. Cold Spring Harbor Laboratory Press, Cold Spring Harbor, N.Y. USA, 1989) and subsequent optical evaluation using corresponding software for concentration determination (Lohaus and Meyer (1989) Biospektrum, 5: 32-39; Lottspeich (1999), Angewandte Chemie 111: 2630-2647).

If the recombinant expression is effected by increasing the synthesis of a protein, then, for example, the number of copies of the corresponding genes is increased or the promoter and regulation region or the ribosome binding site upstream of the structural gene is mutated. By inducible promoters, it is, in addition, possible to increase the expression at any desired time point. In addition, however, it is also possible to assign to the protein gene, as regulatory sequences, what are termed enhancers, which likewise effect increased gene expression via improved interaction between RNA polymerase and DNA. The expression is likewise enhanced by measures for increasing the lifetime of the mRNA.

For increasing the recombinant expression of the respective genes, episomal plasmids, for example, are used. Plasmids or vectors which come into consideration are, in principle, all embodiments available to those skilled in the art for this purpose. Such plasmids and vectors may be found, e.g., in the company pamphlets from Novagen, Promega, New England Biolabs, Clontech or Gibco BRL. Further preferred plasmids and vectors may be found in: Glover, D. M. (1985), DNA cloning: a practical approach, Vol. I-III, IRL Press Ltd., Oxford; Rodriguez, R. L. and Denhardt, D. T. (eds) (1988), Vectors: a survey of molecular cloning vectors and their uses, 179-204, Butterworth, Stoneham; Goeddel, D. V. (1990), Systems for heterologous gene expression, Methods Enzymol. 185, 3-7; Sambrook, J.; Fritsch, E. F. and Maniatis, T. (1989), Molecular cloning: a laboratory manual, 2nd ed., Cold Spring Harbour Laboratory Press, New York.

The plasmid vector which contains the gene that is to be amplified is then transferred to the desired strain by conjugation or transformation. The conjugation method is described, for example, in Schafer et al., Applied and Environmental Microbiology 60: 756-759 (1994). Methods for transformation are described, for example, in Thierbach et al., Applied Microbiology and Biotechnology 29: 356-362 (1988), Dunican and Shivnan, Bio/Technology 7: 1067-1070 (1989) and Tauch et al., FEMS Microbiology Letters 123: 343-347 (1994). After homologous recombination by means of a cross-over event, the resultant strain contains at least two copies of the gene in question.

It is therefore preferred in the method according to the invention that recombinant microorganisms are used; owing to the good genetic accessibility, the micro-organism is preferably selected from the group of the bacteria, in particular the Gram-negative, particularly from the group containing, preferably consisting of, *E. coli, Pseudomonas* sp., *Pseudomonas fluorescens, Pseudomonas putida, Pseudomonas acidovorans, Pseudomonas aeruginosa, Acidovorax* sp., *Acidovorax temperans, Acinetobacter* sp., *Burkholderia* sp., cyanobacteria, *Klebsiella* sp., *Salmonella* sp., *Rhizobium* sp. and *Rhizobium meliloti*, wherein *E. coli* is particularly preferred.

The cells used in the method according to the invention are likewise a component of the present invention.

Therefore, microorganisms which have been genetically modified in such a manner that they synthesize at least one enzyme oxidizing an organic substance and at least one alkL gene product in an amplified manner, wherein the alkL gene product is synthesized independently of at least one other gene product encoded by the alk operon containing the alkL gene, are subject matter of the present invention.

Preferred oxidizing enzymes in this context are the same oxidizing enzymes which are preferably used in the method according to the invention; the same applies to preferred alkL gene products, preferred gene products encoded by the alk operon containing the alkL gene, preferred organic substances, and also preferred micro-organisms.

A further subject matter of the present invention is the use of an alkL gene product, preferably in a micro-organism, for increasing the oxidation rate of at least one enzyme oxidizing an organic substance, characterized in that the use of the alkL gene product proceeds independently of at least one other gene product encoded by the alk operon containing the alkL gene.

In this context, the oxidation is preferably the oxidation of an organic substance to an aldehyde or an alcohol, in particular to an alcohol. Therefore, in this context, preferably the hydroxylation rate is increased, in particular in the ω-position in carboxylic acids, preferably in relation to the conversion of carboxylic acids and esters thereof to the corresponding ω-hydroxylated compounds, in particular dodecanoic acid, methyl ester to hydroxy-dodecanoic acid, methyl ester. Preferred oxidizing enzymes in this context are the same oxidizing enzymes that are preferably used in the method according to the invention; the same applies to preferred alkL gene products, preferably gene products encoded by the alk operon containing the alkL gene, preferred organic substances and preferred microorganisms.

In the examples discussed hereinafter, the present invention is described by way of example, without the invention, the scope of application of which results from the entire description and the claims, being restricted to the embodiments cited in the examples.

The following figures are a component of the examples:
FIG. 1: *E. coli* plasmid "pBT10_alkL"

EXAMPLES

Comparative Example 1

Expression Vector for the AlkBGT Alkane Hydroxylase System from *Pseudomonas putida* GPo1 without alkL Starting from the pCOM systems (Smits et al., 2001 Plasmid 64: 16-24), the construct pBT10 (Seq ID No. 5) was produced which contains the three components alkane hydroxylase (AlkB), rubredoxin (AlkG) and rubredoxin reductase (AlkT) from *Pseudomonas putida*. For expressing the three genes, the alkBFG gene sequence was placed under the control of the alkB promoter and the alkT gene under that of the alkS promoter.

For simplification of the cloning of alkB and alkG, the gene alkF situated therebetween was amplified and cloned together with alkB and alkG. AlkF is of no importance for the reaction that is to be catalysed.

A more detailed description of the production of the vector pBT10 may be found in WO2009077461.

Example 1

Expression Vector for the AlkBGT Alkane Hydroxylase System from *Pseudomonas putida* GPo1 with alkL In a further approach, the alkL gene was cloned into the alkBFG operon in a targeted manner in order to be able to synthesize it together with the minimum set of enzymes required for the oxidation.

For this purpose, the alkL gene from pGEc47 (Eggink et al., 1987, J Biol Chem 262, 17712-17718) was amplified by PCR.

The primers P1 and P2 used for this purpose, for cloning into the SalI restriction cutting site of the plasmid pBT10, likewise contain SalI restriction cutting sites outside the target sequence. Furthermore, a stop codon was incorporated into the forward primer P1 downstream of the SalI restriction cutting site in order to terminate possible translation of the alkH residues.

```
                                            (Seq ID No. 6)
    P1      ACGCGTCGACCTGTAACGACAACAAAACGAGGGTAG (Seq ID No. 7)
    P2      ACGCGTCGACCTGCGACAGTGACAGACCTG
```

For the amplification, the Finnzyme Phusion polymerase (New England Biolabs) was used.

According to the manufacturer's protocol, 34 µl of H2O, 10 µl of 5× Phusion HF buffer, 1 µl of dNTPs (10 mM each), 1.25 µl of P1, 1.25 µl of P2 (for an end-primer concentration of 0.5 µM), 2 µl of pGEc47 plasmid solution (150 ng/µl) and 0.5 µl of Phusion polymerase were mixed and used for the PCR in thin-walled PCR Eppendorf tubes.

The following PCR program was programmed in accordance with a proposal of the polymerase manufacturer:
[98° C./30 sec], ([98° C./10 sec][72° C./60 sec]) 30×, [72° C./10 min]

The resultant PCR product having a length of 754 bp was purified using the "peqGOLD cycle pure Kit" (PEQLAB Biotechnology GmbH, Erlangen) according to the manufacturer's protocol and phosphorylated by T4 polynucleotide kinase. For this purpose, 15 µl of the PCR product solution obtained from the purification were mixed with 2 µl of ATP solution (100 mM), 2 µl of kinase buffer and 1 µl of T4 polynucleotide kinase and incubated for 20 minutes at 37° C. The enzyme was then inactivated by heating it to 75° C. for 10 minutes.

The PCR product thus prepared was then ligated in accordance with the manufacturer's protocol into the pSMART vector from lucigen. 2 µl of the ligation batch were transformed by heat shock (42° C. for 45 sec) into chemically competent DH5α E. coli cells.

After overnight incubation on kanamycin plates, selected colonies were grown overnight at 37° C. in liquid culture (5 ml of LB medium containing 30 µg/ml of kanamycin) and the plasmids were isolated using the peqGOLD Miniprep Kit (PEQLAB Biotechnologie GmbH (Erlangen)).

By restriction cleavage using SalI and subsequent gel electrophoresis, correctly ligated plasmids were identified.

Such a plasmid was prepared in a relatively large amount and cleaved with SalI. The resultant 693 bp fragment was isolated by purification from the agarose gel (peqGOLD Gel Extraction Kit).

The plasmid pBT10 was likewise prepared in a relatively large amount, cleaved with SalI and the ends were dephosphorylated using alkaline phosphatase (calf intestine [alkaline] phosphatase, CIP) (NEB).

These procedures were carried out simultaneously in one reaction tube. For this purpose 13.3 µl of plasmid DNA were mixed with 4 µl of buffer, 19.2 µl of water, 2 µl of alkaline phosphatase and 1.5 µl of SalI (NEB) and incubated for 2 h at 37° C. The cleaved and dephosphorylated vector was likewise purified as described above via an agarose gel.

For setting the correct ratio of vector and insert in the ligation, the concentrations of the corresponding DNA solutions were established by agarose gel electro-phoresis.

For the ligation, 10 µl of cleaved vector-DNA solution were mixed with 5 µl of insert-DNA solution in such a manner that the DNA mass ratio was 1:5, admixed with 2 µl of ligase buffer, 1 µl of water and also 1 µl of ligase, then incubated for 2 h at 22° C. and thereafter overnight at 4° C.

5 µl of this batch were transformed into DH5α E. coli cells by electroporation.

Kanamycin-resistant colonies were grown overnight in 5 ml of LB medium containing antibiotic, and the plasmids were prepared as described above.

Restriction cleavage of the plasmid DNA from 5 clones by EcoRV, in three cases, showed in each case bands at 8248 Bp, 2234 Bp and 1266 Bp. This pattern confirms the correct cloning of alkL.

The resultant plasmid was called pBT10_alkL (see FIG. 1) and has Seq ID No. 8.

Example 2

Conversion of Lauric Acid, Methyl Ester to ω-Hydroxylauric Acid, Methyl Ester

For the biotransformation, the plasmids pBT10 or pBT10_alkL were transformed into the chemically competent strain E. coli. W3110 by heat shock at 42° C. for 2 min (Hanahan D., DNA cloning: A practical approach. IRL Press, Oxford, 109-135). For the synthesis of hydroxylauric acid, methyl ester, E. coli W3110-pBT10 and W3110-pBT10_alkL were cultured over-night at 30° C. and 180 rpm in 100 ml of M9 medium ($Na_2HPO_4$ 6 g/l, $KH_2PO_4$ 3 g/l, NaCl 0.5 g/l, $NH_4Cl$ 1 g/l, 2 mM $MgSO_4$, 0.1 mM $CaCl_2$, 0.5% glucose) containing 30 mg/l of kanamycin and harvested by centrifugation. Some of the biomass was resuspended under sterile conditions in 250 ml of M9 medium containing 0.5% glucose and 30 mg/l of kanamycin to give an OD450=0.2 and further cultured in the shaking flask at 30° C. and 180 rpm. Expression of the alk genes was induced after a growth time of 4 h by adding 0.025% (v/v) of dicyclo-propyl ketone and the culture was shaken for 4 further hours under the same conditions. The cells were then centrifuged off, the cell pellet was resuspended in KPi buffer (50 mM, pH 7.4) and placed in a bioreactor heated to and maintained at 30° C. A biomass concentration of about 1.8 g of CDW/l was set. With vigorous shaking (1500 $min^{-1}$) and an air inflow of 2 vvm (volumes per unit volume and minute), the substrate lauric acid, methyl ester was added to the cell suspension in the ratio 1:2 (100 ml of cell suspension, 50 ml of lauric acid, methyl ester). The temperature was kept constant at 30° C.

Formation of the hydroxylauric acid, methyl ester was detected by GC analysis of the reaction batch. For this purpose, after 0 min as a negative control, and after 150 min, a sample was taken by a syringe by the riser of the reactor and centrifuged in a 2 ml Eppendorf tube in an Eppendorf bench centrifuge for 5 minutes at 13 200 rpm for phase separation. The organic phase was analysed by means of gas chromatography (Thermo Trace GC Ultra). The column used was a Varian Inc. FactorFour™ VF-5 m, length: 30 m, film thickness: 0.25 µm, internal diameter: 0.25 mm.

Analytical Conditions:

| | |
|---|---|
| Oven temperature | 80-280° C. |
| Ramp | 15° C./min |
| Split ratio | 15 |
| Injection volume | 1 µl |
| Carrier flow rate | 1.5 ml/min |
| PTV injector | 80-280° C. at 15° C./s |

Detector Base Temperature: 320° C.

The formation rates measured for 12-hydroxylauric acid, methyl ester can now be converted to the activity of the biocatalyst and related to the cell mass used.

In the linear range of the reaction kinetics, the activity is given by:

activity [U]=converted amount of substance [µmol]/time [min]

This unit "U" which is customary for describing enzymes is a measure of the performance of such a biocatalyst at the start of the reaction.

| Strain | Initial activity [$U/g_{CDW}$] |
|---|---|
| W3110 pBT10 | 1.82 |
| W3110 pBT10_alkL | 48.6 |

The initial activity was increased by the factor 26.7 by the additionally expressed alkL.

The invention claimed is:

1. A genetically modified microorganism capable of oxidizing an organic substance,
wherein the microorganism is genetically modified to synthesize an oxidizing enzyme and an alkane degradation (alk) L gene product,
the alkL gene product is encoded by an alkL gene of *Pseudomonas putida*,
the alkL gene product is provided independently of a second gene product produced from an alk operon comprising the alkL gene in a naturally occurring form,
the second gene product is encoded by at least one gene selected from the group consisting of alkF, alkG, alkH, and alkK genes,
the organic substance is at least one branched or unbranched, saturated or unsaturated, optionally substituted substance selected from the group consisting of an alkane, an alkene, an alkyne, an alcohol, an aldehyde, a ketone, a carboxylic acid, an ester of a carboxylic acid, an amine, and an epoxide, and
the organic substance comprises from 3 to 22 carbon atoms.

2. A method of oxidizing an organic substance, comprising:
bringing in contact the genetically modified microorganism of claim 1 capable of producing an oxidizing enzyme with an organic substance,
wherein the organic substance is at least one branched or unbranched, saturated or unsaturated, optionally substituted substance selected from the group consisting of an alkane, an alkene, an alkyne, an alcohol, an aldehyde, a ketone, a carboxylic acid, an ester of a carboxylic acid, an amine, and an epoxide, and
the organic substance comprises from 3 to 22 carbon atoms.

3. The method of claim 2, wherein the organic substance is at least one selected from the group consisting of a carboxylic acid, an ester corresponding to a carboxylic acid, an unsubstituted alkane comprising from 3 to 22 carbon atoms, an unsubstituted alkene comprising from 3 to 22 carbon atoms, an unsubstituted monohydric alcohol comprising from 3 to 22 carbon atoms, an unsubstituted aldehyde comprising from 3 to 22 carbon atoms, an unsubstituted monobasic amine comprising from 3 to 22 carbon atoms, and a compound substituted by at least one of hydroxyl, amino, keto, carboxyl, cyclopropyl, and epoxy.

4. The method of claim 2, wherein the oxidizing comprises oxidizing the organic substance to an alcohol, to an aldehyde, to a ketone, or to an acid.

5. The method of claim 2, wherein the oxidizing comprises oxidizing the organic substance at an ω-position.

6. The method of claim 2, wherein the oxidizing enzyme is an alkane monooxygenase, a xylene monooxygenase, an aldehyde dehydrogenase, an alcohol oxidase, or an alcohol dehydrogenase.

7. The method of claim 6,
wherein the oxidizing enzyme is an alkane monooxygenase, and
the alkane monooxygenase is a cytochrome-P450 monooxygenase.

8. The method of claim 6,
wherein the oxidizing enzyme is an alkane monooxygenase, and
the alkane monooxygenase is an alkB gene product encoded by an alkB gene from at least one Gram-negative bacterium.

9. The method of claim 6,
wherein the oxidizing enzyme is an alcohol dehydrogenase, and
the alcohol dehydrogenase is encoded by an alkJ gene.

10. The method of claim 2,
wherein the alkL gene product is a protein, and
the protein is encoded by an alkL gene from *Pseudomonas putida* GPo1 or P1 given by Seq ID No. 1 or Seq ID No. 3,
the protein comprises a polypeptide sequence of Seq ID No. 2 or Seq ID No. 4, or
the protein comprises a polypeptide sequence in which up to 60% of amino acid residues are modified in comparison with Seq ID No. 2 or Seq ID No. 4 by deletion, insertion, substitution, or a combination thereof, and has at least 50% of activity of the protein comprising the polypeptide sequence of Seq ID No. 2 or Seq ID No. 4.

11. The method of claim 2,
wherein the organic substance is oxidized with the oxidizing enzyme, the alkL gene product, and a further gene product, and
the further gene product is at least one selected from the group consisting of AlkB, AlkF, AlkG, AlkH, AlkJ, and AlkK.

12. The method of claim 1, wherein the oxidizing is carried out in the microorganism or in a medium surrounding the microorganism.

13. The method of claim 2, further comprising:
synthesizing the oxidizing enzyme and the alkL gene product recombinantly in a microorganism.

14. The method of claim 12,
wherein
the microorganism is a Gram-negative bacterium.

15. The method of claim 2, further comprising:
increasing an oxidation rate of the oxidizing by the alkL gene product,
wherein the increasing proceeds independently of another gene product encoded by the alk operon.

16. The method of claim 5, wherein the organic substance comprises at least one of a carboxylic acid and an ester of a carboxylic acid.

17. The method of claim 7, wherein the cytochrome-P450 monooxygenase is from *Candida* or from a plant.

18. The method of claim 8, wherein the at least one Gram-negative bacterium is a *Pseudomonas*.

19. The method of claim 2, wherein the second gene product is encoded by at least one gene selected from the group consisting of alkF, alkG, and alkH genes.

20. The method of claim 2, wherein the second gene product is encoded by at least one gene selected from the group consisting of alkF, alkG, and alkK genes.

21. The method of claim 2, wherein the second gene product is encoded by at least one gene selected from the group consisting of alkG, alkH, and alkK genes.

22. The method of claim 13, wherein the microorganism is a Gram-negative bacterium.

23. The method of claim 10, wherein the organic substance is selected from the group consisting of a carboxylic acid, an ester corresponding to a carboxylic acid, an unsubstituted alkane comprising from 3 to 22 carbon atoms, an unsubstituted alkene comprising from 3 to 22 carbon atoms, an unsubstituted monohydric alcohol comprising from 3 to 22 carbon atoms, an unsubstituted aldehyde comprising from 3 to 22 carbon atoms, an unsubstituted monobasic amine comprising from 3 to 22 carbon atoms, and a compound substituted by at least one hydroxyl, amino, keto, carboxyl, cyclopropyl, epoxy, or any combination thereof, the oxidizing enzyme is an alkane monooxygenase, a xylene monooxygenase, an aldehyde dehydrogenase, an alcohol oxidase, or an alcohol dehydrogenase, and the method is carried out in a Gram-negative bacterium.

24. The method of claim 23, wherein the Gram-negative bacterium is *Escherichia coli*.

25. The method of claim 23, wherein the organic substance is at least one of lauric acid and esters thereof, and the oxidizing enzyme is cytochrome-P450 monooxygenase or an alkB gene product encoded by an alkB gene from at least one Gram-negative bacterium.

* * * * *